(12) United States Patent
Kennedy, II

(10) Patent No.: US 7,608,056 B2
(45) Date of Patent: Oct. 27, 2009

(54) STEERABLE CATHETER DEVICES AND METHODS OF ARTICULATING CATHETER DEVICES

(75) Inventor: Kenneth C. Kennedy, II, Clemmons, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 318 days.

(21) Appl. No.: 11/588,806

(22) Filed: Oct. 27, 2006

(65) Prior Publication Data

US 2007/0100235 A1    May 3, 2007

Related U.S. Application Data

(60) Provisional application No. 60/731,763, filed on Oct. 31, 2005.

(51) Int. Cl.
*A61M 31/00* (2006.01)
*A61M 37/00* (2006.01)

(52) U.S. Cl. .................. 604/95.03; 604/525; 604/527
(58) Field of Classification Search .......... 604/95.03, 604/96.01, 97.01, 98.01, 102.03, 524–528, 604/530, 532, 536, 95.01, 95.02, 95.04, 523
See application file for complete search history.

(56) References Cited

U.S. PATENT DOCUMENTS 3,773,034 A    11/1973    Burns et al.
(Continued)

FOREIGN PATENT DOCUMENTS

FR    2 577 789 A1    2/1985

OTHER PUBLICATIONS

Written Opinion, dated Jan. 10, 2008, for International Application No. PCT/US2006/042490.
(Continued)

*Primary Examiner*—Nicholas D Lucchesi
*Assistant Examiner*—Nathan R Price
(74) *Attorney, Agent, or Firm*—Brinks Hofer Gilson & Lione

(57) ABSTRACT

Steerable catheter devices are provided having a proximal first end portion, an elongate intermediate portion, and a distal flexible second end portion defining a longitudinal axis, and at least one channel having a proximal opening and terminating at an occluded distal end radially offset relative to the central longitudinal axis and positioned within the catheter flexible second end portion substantially straight in a relaxed position and bent when the occluded distal end is under a change in internal fluid pressure. Optionally, the catheter further has a dye injection lumen and a tool receiving passageway extending from the first end portion to the second end portion. The occluded distal end is axially elastically distensible under an internal fluid pressure to deflect (thereby to steer) the catheter second end portion through the tortuous path of a vessel passageway when used percutaneously or working channel of an endoscope or endoscope accessory device.

16 Claims, 11 Drawing Sheets

U.S. PATENT DOCUMENTS

| | | |
|---|---|---|
| 4,403,985 A | 9/1983 | Boretos |
| 4,794,912 A | 1/1989 | Lia |
| 4,909,787 A | 3/1990 | Danforth |
| 5,123,421 A | 6/1992 | Sinofsky |
| 5,314,428 A * | 5/1994 | Marotta .................. 604/95.03 |
| 5,619,993 A | 4/1997 | Lee |
| 6,299,599 B1 * | 10/2001 | Pham et al. ................. 604/113 |
| 7,101,362 B2 | 9/2006 | Vanney |
| 2004/0127849 A1 * | 7/2004 | Kantor .................. 604/102.03 |
| 2004/0186378 A1 | 9/2004 | Gesswein |
| 2007/0060997 A1 * | 3/2007 | de Boer .................... 623/1.11 |

OTHER PUBLICATIONS

Search Report and Written Opinion dated Mar. 1, 2007, for International Application No. PCT/US2006/042490.

* cited by examiner

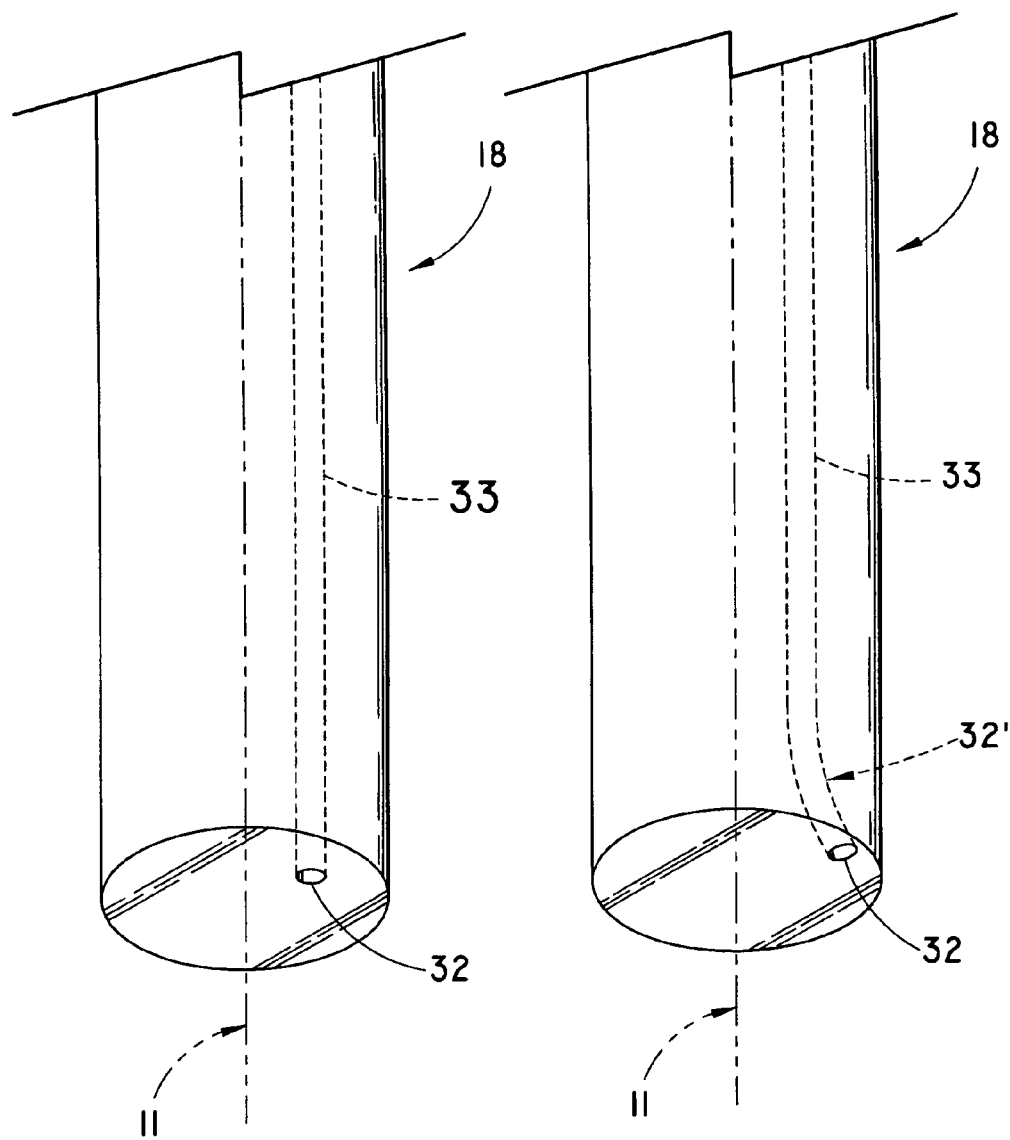

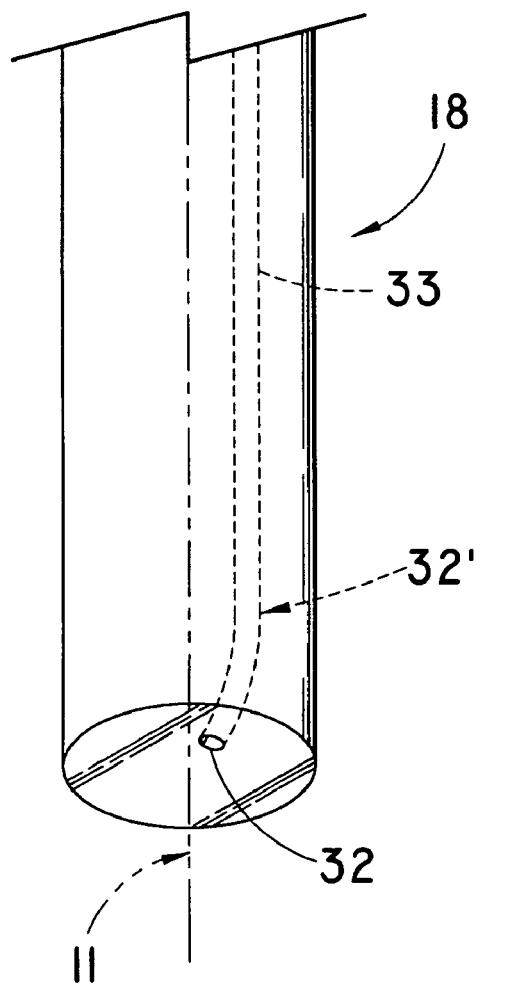
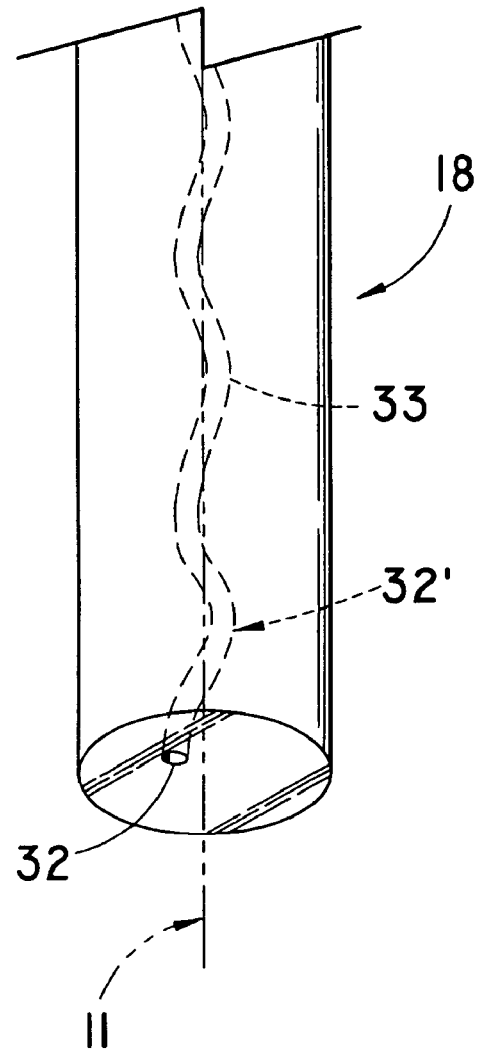
FIG. 3C
FIG. 3D

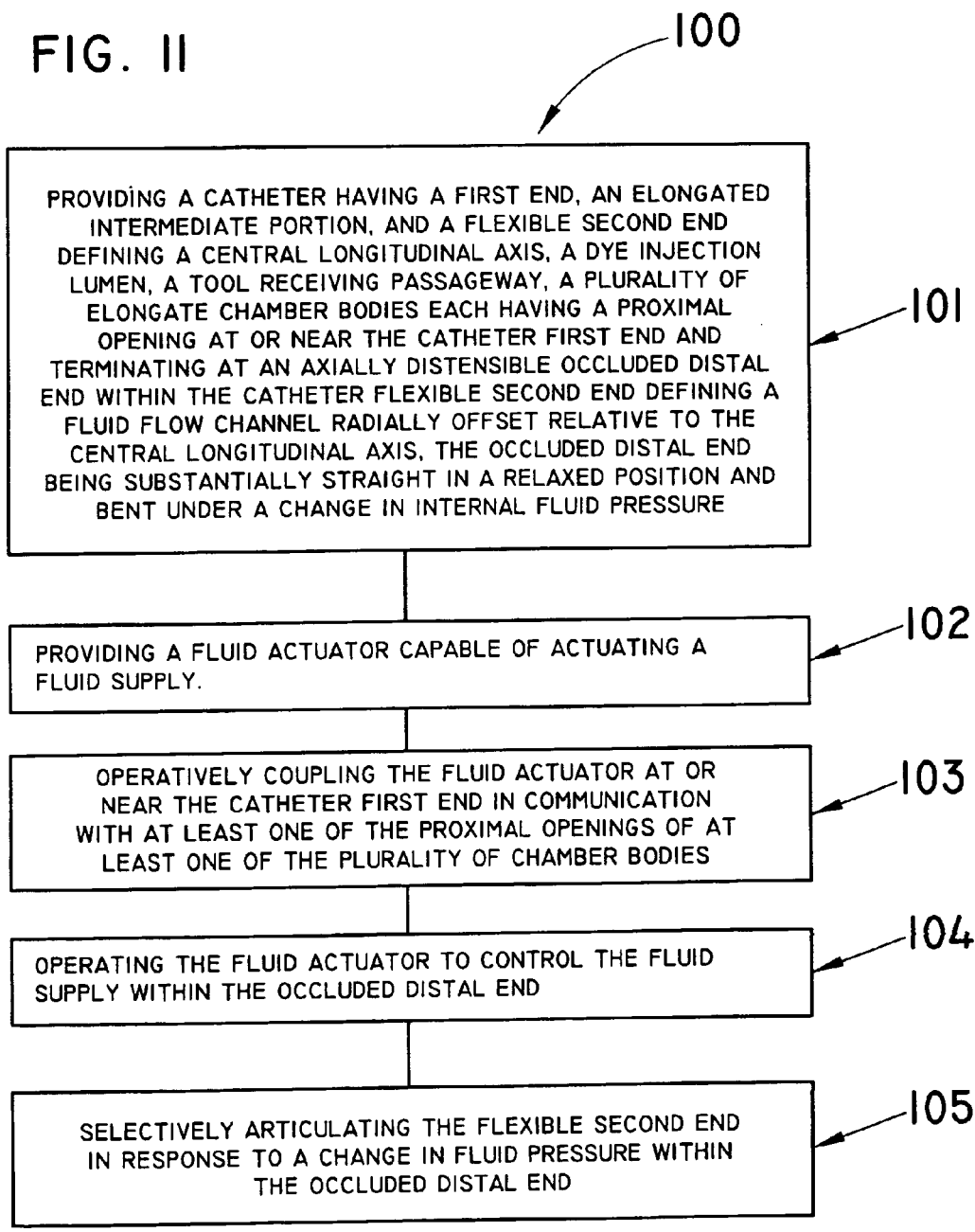

STEERABLE CATHETER DEVICES AND METHODS OF ARTICULATING CATHETER DEVICES

RELATED APPLICATIONS

The present patent document claims the benefit of the filing date under 35 U.S.C. §119(e) of U.S. Provisional Patent Application filed on Oct. 31, 2005 entitled, "Steerable Catheter Devices and Methods of Articulating Catheter Devices," and having an application Ser. No. 60/731,763, the disclosure of which is hereby incorporated by reference in its entirety.

FIELD OF THE INVENTION

The present invention relates to catheter devices for use with endoscopes or percutaneously with vascular medical devices and the like, wherein the catheters employ fluids used to steer the distal tip of the catheter.

BACKGROUND OF THE INVENTION

Physicians and other healthcare professionals (collectively, "physician") commonly use catheters in a variety of medical procedures. Catheters guide and introduce a variety of medical devices, guide wires, drug delivery tools, therapeutic agents (e.g., drugs, medication, narcotics, antibiotics, pharmaceutical products, and/or medicinal agents, therapies, or substances) and other operative instruments or devices (individually and collectively, "instruments") into the body percutaneously or through a working channel of an endoscope or accessory channel to be used with an endoscope. Thus, catheters often serve as a highway—a temporarily established path—for placing, introducing, exchanging, and replacing instruments during a medical procedure, thereby eliminating the need for performing delicate navigation procedures for each instrument passed into a vessel passageway.

A vessel passageway includes any lumen, chamber, channel, opening, bore, orifice, flow passage, duct, organ, or cavity for the conveyance, regulation, flow, or movement of bodily fluids and/or gases of an animal. For example, physicians frequently use catheters in medical procedures that involve the passageways of a heart, blood vessel, artery, vein, capillary, bronchiole, brachial, trachea, esophagus, aorta, intestine, bile duct, pancreas, liver, gall bladder, ureter, urethra, fallopian tube, and other locations in a body (collectively, "vessel") to name a few. Similarly, physicians may place catheters through a working channel of an endoscope, or a channel endoscope accessory device, during endoscopic medical procedures that involve these vessel passageways.

In order to negotiate a typically tortuous path of a vessel passageway or to avoid obstacles during insertion of a catheter through vessel passageways, conventional catheters include hollow flexible tubes with a tactile first end and a flexible second end. The first end forms the end that physicians sometimes grip or otherwise secure, and the second end forms the end that physicians position at or near the target site. The hollow tube normally comprises a substantially circular cross section to mimic the configuration of a typical vessel passageway or the channel of an endoscope or endoscope accessory device.

Maneuvering the catheter second end through the vessel passageway and to the target site often presents a time-consuming endeavor for the physician. In order to obtain a desired maneuverability of the second end, conventional catheters commonly employ one of several approaches and features.

In one type of catheter, the second end moves substantially passively. As the physician inserts the catheter through the vessel passageway, the catheter follows the path of the vessel passageway. Should this catheter enter the wrong vessel opening, such as in a case of a bifurcated vessel pathway, the physician must engage in a series of steps of manually withdrawing the second end from the wrong vessel opening, and then reinserting the second end until it enters the desired opening. In order to accomplish this feat, the physician may also rotate the catheter about the catheter longitudinal axis. A physician may need to make numerous attempts with the passive catheter to gain access through the desired opening. Any of these steps increases the length of time for the medical procedure and possibly patient discomfort.

The present inventions solve these and other problems with a steerable distal second end portion and/or sterrable distal tip.

In another type of catheter, the catheter second end may include a slight pre-formed bend. Thus, the catheter second end follows closer to the wall of the vessel passageway than it does the center of the vessel passageway. Upon encountering a choice of taking two or more vessel openings (again using a bifurcated vessel pathway as an example), the physician rotates the catheter about the catheter longitudinal axis until the catheter second end points toward the desired opening. These catheters require a certain amount of torque-ability, however, which refers to the extent to which a catheter transfers a torque in a one-to-one relationship from the first end to the second end without a whipping effect resulting from torque build-up in the catheter. Also, as the catheter is inserted deeper and deeper into a patient, and as the catheter navigates through a tortuous pathway of vessel openings, catheter rotation may become more difficult and may present the patient with some discomfort.

The present inventions solve these and other problems with a steerable distal second end portion and/or steerable distal tip that are substantially straight in a relaxed portion and articulates from a relaxed position to a bending position.

In yet another type of catheter, cables within the catheter help to maneuver the catheter second end. These cables typically comprise a wire having a first end attached to the catheter first end, and a second end attached to the catheter second end. The physician actuates one or more cables by pulling proximally, pushing distally, or rotating the one or more cable first ends, which translates a corresponding movement in the cable second ends and, as a result, the catheter second end. As is conventional, "distal" means away from the operator when the device is inserted into a patient, while "proximal" means closest to or toward the operator when the device is inserted into a patient. Maneuvering a catheter with cables requires a catheter having two competing criterion. The catheter must be sufficiently flexible to avoid damaging the vessel through which the physician advances the catheter. Conversely, the cable must have suitable column strength sufficient to allow the cable to be pushed, pulled, and rotated through the endoscope channel or a patient's vessel passageway. Moreover, a cable typically extends through a substantial length of the catheter, which cable length tends to increase the variable that the catheter may kink, buckle, bow, or prolapse as a result of the tortuous path the procedure may require.

The present inventions solve these and other problems with a steerable distal second end portion and/or steerable distal tip that have an elastically fluid-distensible occluded distal end offset from a substantially central longitudinal axis.

Other catheters might consider employing fluid force to steer the catheter with a fluid actuating lumen that extends the length of the catheter. One problem they would have with fluid forced steerable catheters is the tendency to balloon the fluid actuating lumen as fluid is forced through the actuating lumen to the distal end. Forcing fluid through the actuating lumen causes the lumen to expand radially (balloon) along the length of the actuating lumen, thereby reducing the fluid force in the longitudinal direction such that there is inadequate fluid force at the distal end to cause the catheter to bend.

The present inventions solve these and other problems by having a larger outer diameter (hence, greater thickness to transmit fluid force) that steps down to a smaller outer diameter at the steerable distal second end portion and/or steerable distal tip.

Other problems one would have if considering a fluid forced catheter is radial ballooning of the actuating lumen at the sealed distal end that is intended to cause the catheter to bend. The present invention solves these and other problems with an expansion resistant outer reinforcement.

Also, one considering fluid force for a steerable catheter would, given the problem with collapsing inward, limit the functionality of the steerable catheter to steering and possibly a small lumen for contrast fluid. As a result, their catheters would only be usable for placing, introducing, exchanging, or replacing instruments having a central lumen that may pass over the catheter in a back-loaded or front-loaded medical procedure. Consequently, the catheters would not be replaceable with a wire guide.

The present invention solves these and other problems with a fluid forced catheter adapted with a tool receiving passageway disposed with the catheter and extending to a steerable distal second end portion. Additionally, the passageway may have a compression resistant inner reinforcement.

It is therefore desirable to provide an alternative to the above-described conventional catheters that eliminates or reduces one or more of the limitations or disadvantages discussed above.

SUMMARY OF THE INVENTION

The present invention provides steerable catheter devices for use with endoscopes or percutaneously through vessel passageways and body cavities. In particular, the present invention provides a catheter that utilizes fluids to maneuver the flexible second end portion. Moreover, fluids are especially suitable to percutaneous and endoscopic surgical procedures because fluids allow for work over long distances in a flexible arrangement without any substantive increased in the tendency toward kinking, buckling, bowing, or prolapse. As taught herein, steerable catheter devices and methods of articulating catheter devices are provided.

In one embodiment, the device includes a catheter having a first end portion and a flexible second end portion. A chamber body extends from a proximal opening at or near the catheter first end portion to an occluded distal end at or near the catheter flexible second end portion, and defines a channel therebetween. The occluded distal end is elastically distensible under an internal fluid pressure for articulating the catheter flexible second end portion.

Another embodiment includes a catheter having an elongated intermediate portion extending from a first end portion to a flexible second end portion and defining a central longitudinal axis. The flexible second end portion comprises a steerable distal tip portion. Two or more elongate chamber bodies are arranged about the longitudinal axis, with each of the two or more chamber bodies having a fluid flow channel from a proximal opening located at or near the first end portion and terminating at a distensible occluded distal end located at or near the steerable distal tip portion. A fluid actuator operably connects at or near the first end portion and is in communication with at least one of the proximal openings of the fluid flow channels, and is capable of controlling a supply of fluid to and from the at least one fluid flow channel. In response to a change in fluid pressure, the distensible occluded distal end is capable of articulating the steering tip portion.

Methods of orienting a surgical access catheter device are also provided. In one embodiment, a method according to the invention comprises providing a catheter having a first end and a second flexible end and two or more chamber bodies having a proximal opening at or near the catheter first end, a distensible occluded distal end at or near the catheter flexible second end, and defining a channel therebetween. A fluid actuator capable of controlling a supply of fluid is provided and connected at or near the catheter first end in operable communication with at least one of the proximal openings of at least one of the two or more chamber bodies. The fluid actuator is operated to control the fluid supply within the occluded distal end and selectively articulate the shaft flexible second end in response to a change of fluid pressure within the occluded distal end.

BRIEF DESCRIPTION OF THE DRAWINGS

Embodiments of the present invention will now be described by way of example, and not by way of limitation, with reference to the accompanying drawings briefly described as follows:

FIG. 3A provides a perspective partial view, broken away, of a chamber body of a flexible second end portion of an embodiment of the invention.

FIG. 3B provides a perspective partial view, broken away, of an alternative embodiment of a chamber body of a flexible second end portion.

FIG. 3C provides a perspective partial view, broken away, of another embodiment of a chamber body of a flexible second end portion.

FIG. 3D provides a perspective partial view, broken away, of still another embodiment of a chamber body of a flexible second end portion.

FIG. 11 is a block diagram illustrating a method of the invention.

DESCRIPTION OF EMBODIMENTS

Although not limited in its scope or applicability, the present inventions relate generally to steerable catheter devices used percutaneously, through an endoscope working channel, or through an accessory channel used with an endoscope. More particularly, and by way of illustration and not by way of limitation, the present inventions relate to steerable catheter devices comprising one or more channels having an occluded distal end at or near a flexible second end portion of the catheter. The occluded distal end distends axially under an internal fluid pressure, and thereby deflects and steers the device.

For the purpose of promoting an understanding of the principles of the invention, the following provides a detailed description of embodiments of the invention as illustrated by the drawings as well as the language used herein to describe the aspects of the invention. The description is not intended to limit the invention in any manner, but rather serves to enable those skilled in the art to make and use the invention. As used herein, the terms comprise(s), include(s), having, has, with, contain(s) and variants thereof are intended to be open ended transitional phrases, terms, or words that do not preclude the possibility of additional steps or structure.

Figure 1:
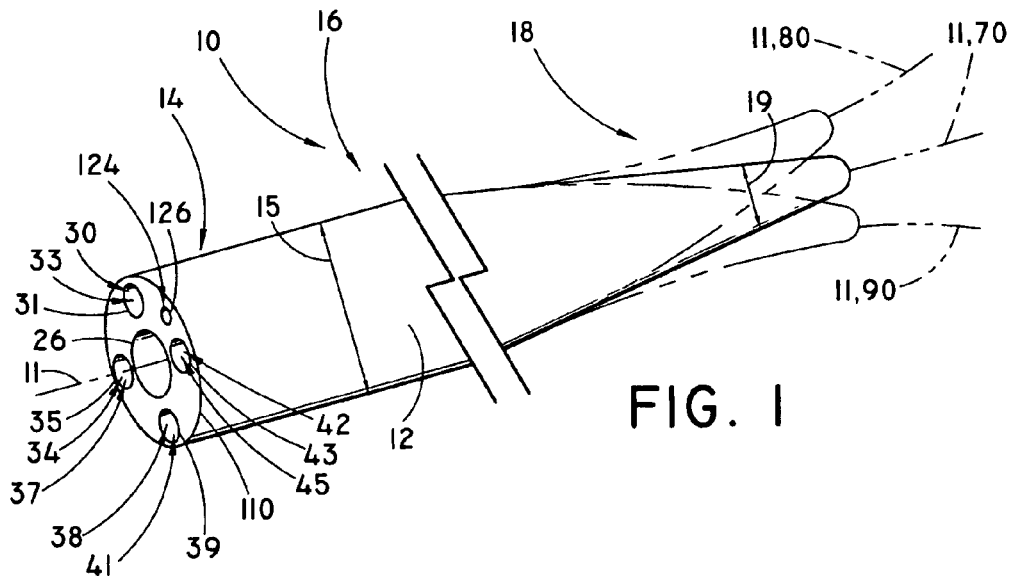
FIG. 1 provides a perspective view, broken away, and taken in a distal direction, of a steerable catheter device according to one embodiment of the invention.

FIG. 1 illustrates a steerable catheter device 10 according to an embodiment of the present invention. The steerable catheter device 10 comprises a catheter 12 having a proximal first end portion 14 and a flexible distal second end 18, and an elongate intermediate portion 16.

In describing an embodiment of the invention, the term "catheter" shall have its plain and ordinary meaning, rather than any lexicographic definition. Given the configuration of a vessel passageway or the channel of an endoscope or accessory device, a variety of catheters 12 of different shapes and sizes can be used depending on the particular medical applications for the catheter. For instance, an embodiment of a suitable catheter 12 for a steerable catheter assembly comprises a tubular member, which may be better tolerated by the patient to minimize pain and discomfort than other configurations. The term "tubular" in describing this embodiment includes any tube-like, cylindrical, elongated, shaft-like, rounded, oblong, or other elongated longitudinal shaft extending between a first end 14 portion and a second end portion 18 and defining a substantially central longitudinal axis 11 at the second end portion 18 and/or at a steering tip portion 22 (discussed below). As used herein and throughout to describe embodiments of the invention, the "central longi-tudinal axis" (or just "longitudinal axis") describes the approximate central longitudinal lengthwise axis of the catheter's flexible second end portion 18 and/or steering tip portion 22. The central longitudinal axis 11 may be straight or may at times even be curved, because as explained below, the second end portion 18 and steering tip portion 22 are flexible. The first end portion 14 and intermediate portion 16 may also be flexible. Furthermore, the longitudinal axis 11 is substantially central to the extent that it need not be central to a mathematical certainty—just approximately central.

Similarly, the dimensions of the catheter will depend on various factors. These factors include the intended use of the catheter and the vessel passageway or the channel of an endoscope or accessory device into which the catheter will be positioned. In general, however, the catheter is elongate, meaning that it is relatively long enough to reach a target site at a region internal the patient's body. The overall catheter length may vary greatly, however, depending on the intended medical procedure for the device and the location of the target site internal the patient's body. In one embodiment, the length of the catheter 12 may be in the range of between about 50 centimeters ("cm") and about 600 cm, although the length of the catheter may be shorter or longer as desired. Alternatively, the length may range from about 100 cm to about 480 cm. For a catheter intended to be used in a common bile duct, one example of a suitable length may be in the range from approximately 175 to approximately 225 cm.

Just as the catheter length may vary, so, too, the catheter outer diameter also may vary along the length of the catheter. In one embodiment, the catheter may have a substantially constant outer diameter. In another embodiment, the catheter first end portion 14 and/or elongate intermediate portion 16 includes an optional first outer diameter 15 while the catheter second end portion 18 (or steering tip portion 22) includes an optional second outer diameter 19 relative to the first outer diameter 15. The second diameter 19 is smaller than the first diameter 15. Optionally, the catheter 12 may generally taper (larger to smaller) from the first end portion 14 to the second end portion 18 and/or steering tip portion 22. In contrast, the diameter of a catheter 12 need not taper but may increase at any region or point along the length of the catheter from the first end portion 14, the intermediate portion 16, and the second end portion 18. For instance, in one embodiment, the first outer diameter 15 is substantially uniform (or may comprise a gradual taper) from the first end portion 14 through the elongate intermediate portion 16 which then steps down to a smaller second outer diameter 19 that is located at or near the catheter second end portion 18 and/or steering tip portion 22. In one embodiment, by way of illustration only, the first outer diameter 15 may be in the range from between about 1.0 to about 5.0 millimeters ("mm") (although the diameter may be lesser or greater than this range), while the second outer diameter 19 may be in the range from between about 0.5 mm and about 2.0 mm.

As shown in FIG. 1, the catheter second end portion 18 is flexible. The second end portion 18 is articulatable (described below) from a relaxed (e.g., neutral, approximately equal pressure) position 70 to a bending position 80, 90 (e.g., FIGS. 1 and 9). Although the first end portion 14 also may be flexible, the first end portion 14 typically exhibits less flexibility, or may even be rigid or semi-rigid, relative to the second end portion 18. Indeed, the first end portion 14 may be rigid if it extends outside the patient's body, but flexible where it is to be inserted into the patient (which includes a patient's vessel passageway; or the channel of an endoscope or endoscope accessory device to be inserted into the patient's vessel passageway). Moreover, the elongate intermediate portion 16 is flexible where it is to be inserted into the patient so that it may navigate through bends and turns of the vessel passageway, the endoscope working channel, or the endoscope accessory channel.

The catheter 12 may be purchased. In the alternative, the catheter may be made by any methods of extrusion, pultrusion, injection molding, transfer molding, flow encapsulation, fiber winding on a mandrel, or lay-up with vacuum bagging, to name a few. A variety of suitable materials may be used, so long as the flexible sections of the intermediate portion 16 and the second end portion 18 comprise materials that allow desired flexibility. For example, suitable materials include surgical stainless steel or biologically compatible metals, polymers, plastics, alloys (including super-elastic alloys), or composite materials that are either biocompatible or capable of being made biocompatible. The flexible sections of the intermediate portion 16 and/or the second end portion 18 may be made of any suitable material (natural, synthetic, plastic, rubber, metal, or combination thereof) that is strong yet flexible and resilient comprising, for by way of illustration and not by way of limitations, elastomeric materials such as and including any latex, silicone, urethane, thermoplastic elastomer, nickel titanium alloy, polyether etherketone ("PEEK"), polyimide, polyurethane, cellulose acetate, cellulose nitrate, silicone, polyethylene terephthalate ("PET"), polyamide, polyester, polyorthoester, polyanhydride, polyether sulfone, polycarbonate, polypropylene, high molecular weight polyethylene, polytetrafluoroethylene ("PTFE"), or mixtures or copolymers thereof, polylactic acid, polyglycolic acid or copolymers thereof, polycaprolactone, polyhydroxyalkanoate, polyhydroxy-butyrate valerate, polyhydroxy-butyrate valerate, or another polymer or suitable material.

In one embodiment, the flexible second end portion 18, a steering tip portion 22 (discussed below), and elastically fluid-distensible occluded distal ends 32, 36, 40, and 44 (discussed below) may comprise an optional anisotropic material that is, or can be made to be, relatively compliant in an axial direction as compared to a transverse direction. This characteristic is known generally as "anisotropy" (in contrast to "isotropy" where the material characteristics are uniformly independent of direction or orientation within the material). In one embodiment of the invention that uses optional anisotropic material, the specific anisotropic behavior would be achieved by circumferentially reinforcing the second end portion 18 and/or steering tip portion 22 so that its "hoop" stiffness (e.g., circumferential stiffness) is higher than its axial stiffness. This could be accomplished by a variety of methods, one of which would be to wrap or wind reinforcing fibers around the second end portion 18 and/or steering tip portion 22, or to embed them circumferentially within the material. Consequently, suitable pressurization or depressurization to elongate chamber bodies 30, 34, 38, 42 would generate forces within the material that result in desired distention and articulation, as discussed below.

In the axial direction, the specific type of elastic behavior will have an impact on articulation, too. If a truly elastomeric material is used (like a rubber), which by definition has a distensibility in the range of 200%-800%, then a relatively short chamber body 30, 34, 38, 42 will be capable of generating a relatively large angular deflection, resulting in a sharp (short radius) turn. If a typical substantially non-elastomeric material is used (e.g., conventional catheter materials) then a relatively long chamber would be necessary in order to achieve large angular deflections. The result in that case would be a large-radius bend at the second end portion 18 and/or steering tip portion 22. Large angular deflections, however, may not be necessary in order to cause significant articulation to a catheter device. Deflections of a few degrees may be all that a physician requires in order to navigate a catheter to a particular branch a branch, vessel, or vessel passageway.

For those portions of the catheter 12 that will not contact the patient (e.g., it is contained within a sheath, working channel of an endoscope, or an external accessory channel device used with an endoscope), the catheter 12 material need not be biocompatible. In contrast, where there is the possibility of patient contact, such as with the catheter second end portion 18, then the material may need to be biocompatible or capable of being made biocompatible, such as by coating, chemical treatment, or the like.

Optionally, a thin PTFE heat shrinkable material coats the catheter 12. The heat shrinkable nature of these materials facilitates manufacturing while providing a lubricious coating, which facilitates navigation. The thickness of the coating may vary between approximately 0.01 mm and approximately 0.20 mm. In another embodiment, the coating thickness may very between approximately 0.01 mm and approximately 0.05 mm. Alternatively, the coating may have a thickness between approximately 0.01 mm and approximately 0.02 mm. These thicknesses provide suitable coatings while not adding significantly to the overall thickness of the device. The coating may be applied to a substantial portion of the length of the catheter. In another alternative, the coating may be applied at least to a substantial portion of the second end portion 18 to be inserted into the vessel passageway, endoscope working channel, or an accessory channel used with an endoscope. With or without the PTFE coating, the catheter or insertion portion of the catheter may be treated with a hydrophilic coating or hybrid polymer mixture. Such materials comprise any suitable polyvinyl puroladine and cellulose esters in organic solvent solutions. These solutions make the catheter surface particularly lubricious when in contact with body fluids, which aids in navigation.

Radiopaque materials and markers such as bismuth or gold may be added to the coating. Also, the second end portion 18 and/or steering tip portion 22 may further comprise radiopaque materials and markers, and for instance, by being used with, placed on, or otherwise embedded in, attached to, or formed into the second end portion 18 and/or steering tip portion 22. Several examples of suitable radiopaque materials and markers are known in the art, and any suitable material and/or marker can be utilized in the present invention.

One use of an embodiment of the invention may be, by way of example only and not by way of limitation, endoscopic retrograde cholangiopancreatography ("ERCP"), which enables the physician to diagnose problems in the liver, gallbladder, bile ducts, and pancreas. The liver is a large organ that, among other things, makes a liquid called bile that helps with digestion. The gallbladder is a small, pear-shaped organ that stores bile until it is needed for digestion. The bile ducts are tubes that carry bile from the liver to the gallbladder and small intestine. These ducts are sometimes called the biliary tree. The pancreas is a large gland that produces chemicals that help with digestion and hormones such as insulin.

ERCP is used primarily to diagnose and treat conditions of the bile ducts, including gallstones, inflammatory strictures (scars), leaks (from trauma and surgery), and cancer. ERCP combines the use of x rays and an endoscope. The endoscope for the ERCP procedure has a proximal control section remains outside the patient during a medical procedure and has a distal insert portion comprising a long, flexible, lighted tube with a means for viewing the inside of the patient through a viewing lens disposed at the insert portion. Other common features of an endoscope for ERCP include a working channel for passing a tool, a light guide cable, and a power supply.

During the ERCP procedure, the patient will often be positioned on the patient's side in order to swallow the insert portion of the endoscope, and the physician will then guide the insert portion through your esophagus, stomach, and duodenum until it reaches the spot where the ducts of the biliary tree and pancreas open into the duodenum. Sometimes the more challenging part of the ERCP procedure is deep cannulation of the biliary duct. In other words, the physician needs to move the insert portion of the endoscope through the main entry of the ducts. Because the network of ducts present tight passageways that are too small for the insert portion of the endoscope, the patient may be turned to lie flat on his or her stomach and a catheter passed through the working channel of the endoscope. Where the endoscope stops, the catheter may exit the working channel and then move through the network of the biliary tree; so that this is not done blindly there may be injection dye/contrast agents released to the biliary tree. When the catheter reaches the diseased area, it may be helpful to replace the catheter with a wire guide for passing other instruments to the diseased area.

Figure 2:
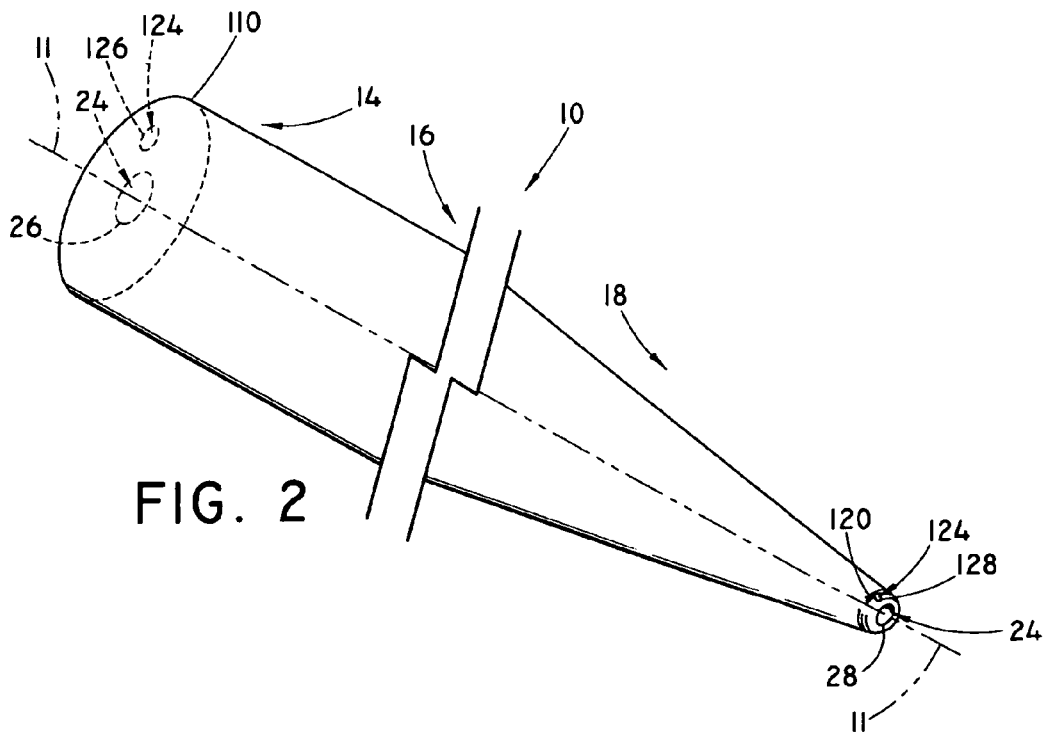
FIG. 2 provides a perspective view, broken away, taken in a proximal direction, of a steerable catheter device according to FIG. 1.

FIGS. 1 and 2 show embodiments of the invention wherein the catheter has an injection lumen 124 through which dyes and contrast agents may be injected into the ducts ("a dye injection lumen 124" or "injection lumen 124"). The injection lumen 124 comprises a proximal end opening 126 located at the catheter first end portion 14 and a distal end opening 128 located at the catheter second end portion 18. Through the injection lumen 124, the physician will inject a dye into the ducts to make them show up clearly on x rays. X rays are taken as soon as the dye is injected. Using the X rays, the physician can see the inside of the biliary tree and/or pancreas so that the physician can guide the catheter inside the patient toward the target site.

Other catheters might consider employing fluid force to steer the catheter with a fluid actuating lumen that extends the length of the catheter, but the problem lies in the catheter having only an injection lumen. This lumen cannot be used for both injecting the dyes and as a tool receiving passageway for receiving a wire guide, by way of example. Indeed, the injection lumen may be too small to receive the wire guide. In a case where an injection lumen is configured to receive the wire guide, then the problem is twofold. First, if the fit is too tight then the injection dye/contrast agent can no longer pass through the injection lumen. Second, if the fit is not tight enough, then the injection lumen cannot form a proper seal at the proximal end of the catheter for the purposes of forcing dye and contrast fluid to the diseased area. Thus, there needs to be a separate tool receiving passageway so that the fluid forced steerable catheter can be replaced by, for instance, a wire guide to be manipulated through the patient or used as a highway of sorts for passing other instruments to the diseased area. The present inventions solve this and other problems with a separate tool receiving passageway in order to provide additional functionality to the steerable fluid forced catheter. With the tool receiving passageway, however, the catheter of a fluid forced steerable catheter may become unstable and prone to radial compression. This and other problems are also solved by the present invention as taught below.

In FIGS. 1 and 2, the first end portion 14 of the catheter 12 comprises an outer circumference 110 relative to the central longitudinal axis 11. The second end portion 18 of the catheter comprises an outer circumference (see FIG. 2) relative to the central longitudinal axis 11. The second end portion 18 of the catheter comprises an outer circumference 120 (see FIG. 2) relative to the central longitudinal axis 11, wherein the second end outer circumference 120 is smaller than (e.g., less than, reduced dimension, not as large as) the first end outer circumference 110.

FIGS. 1 and 2 further show an embodiment of a catheter 12 having an optional tool receiving central passageway 24 extending from a proximal end opening 26 formed at or near the first end portion 14 of the catheter 12 to a distal opening 28 formed at or near the flexible second end portion 18. The second end opening 28 is oriented toward a space exterior to the second end portion 18; in other words, it is at the distal end face of the second end portion 18 (as opposed to the side of the second end portion 18 wherein the opening 28 is transverse to the central longitudinal axis 11) in one embodiment of the invention. The distal end face may be planar, flat, rounded, chamfered, distally tapered, or arrow-head shape that may be better tolerated by the patient to minimize pain and discomfort.

Depending on the intended use for the device and the particular medical procedure to be performed, the passageway 24 of a steerable catheter may comprise a passageway extending along the longitudinal axis 11 from the proximal first end opening 26 to the distal second end opening 28. The term "passageway" in describing these embodiments of a steerable catheter or steerable catheter assembly may be any lumen, channel, flow passage, duct, chamber, opening, bore, orifice, or cavity for the conveyance, regulation, flow, or movement of or the passage of number of devices for use with the steerable catheter assembly. For example, these devices may include diagnostic, monitoring, treatment, operating instruments, tools, accessories, and therapeutic delivery devices (collectively, "tools"). One such tool may be a wire guide (also known as a guide wire). Therefore, the passageway is a tool receiving passageway. In one embodiment, the tool receiving passageway is a central passageway, which should be understood to be a passageway approximately extending along and co-axial with the longitudinal axis 11 from the second end distal opening 28 to about the first end proximal opening 24.

The second end opening 28 of the tool receiving central passageway 24 is substantially coaxial with the central longitudinal axis 11 and oriented longitudinally toward a space distally exterior to the second end portion 18 substantially along the longitudinal axis 11 beyond the end face of the second end portion 18. This is advantageous for passing a tool (e.g., a wire guide) in a preferred embodiment wherein the flexible distal second end portion is substantially straight in the relaxed position. In other words, the tool may enter or exit without going through any sharp turn as it must do if the second end opening 28 were on the sidewall (e.g., circumference 120) and subjecting the wire guide to kinking, buckling, prolapsing, recoiling, and the like (collectively, "kinking"). Indeed, a pre-bent second end portion is easier to deform once at the target site within the patient, but the straightened second end portion 18 and/or steering tip portion 22 overcomes problems, such as whipping, that are inherent in the precurved second end portion in getting the second end portion 18 and/or steering tip portion 22 positioned at the target site.

Figure 2A:
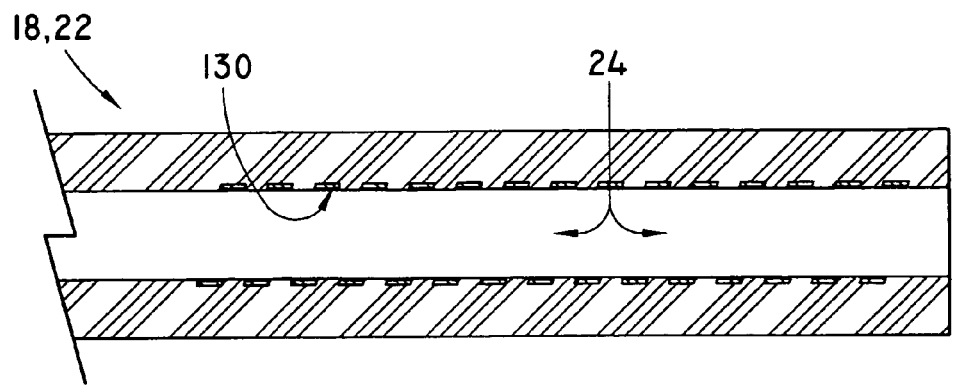
FIG. 2A provides a perspective view of a steerable catheter device having a compression resistant inner reinforcement according to one embodiment of the invention.
Figures 8, 9:
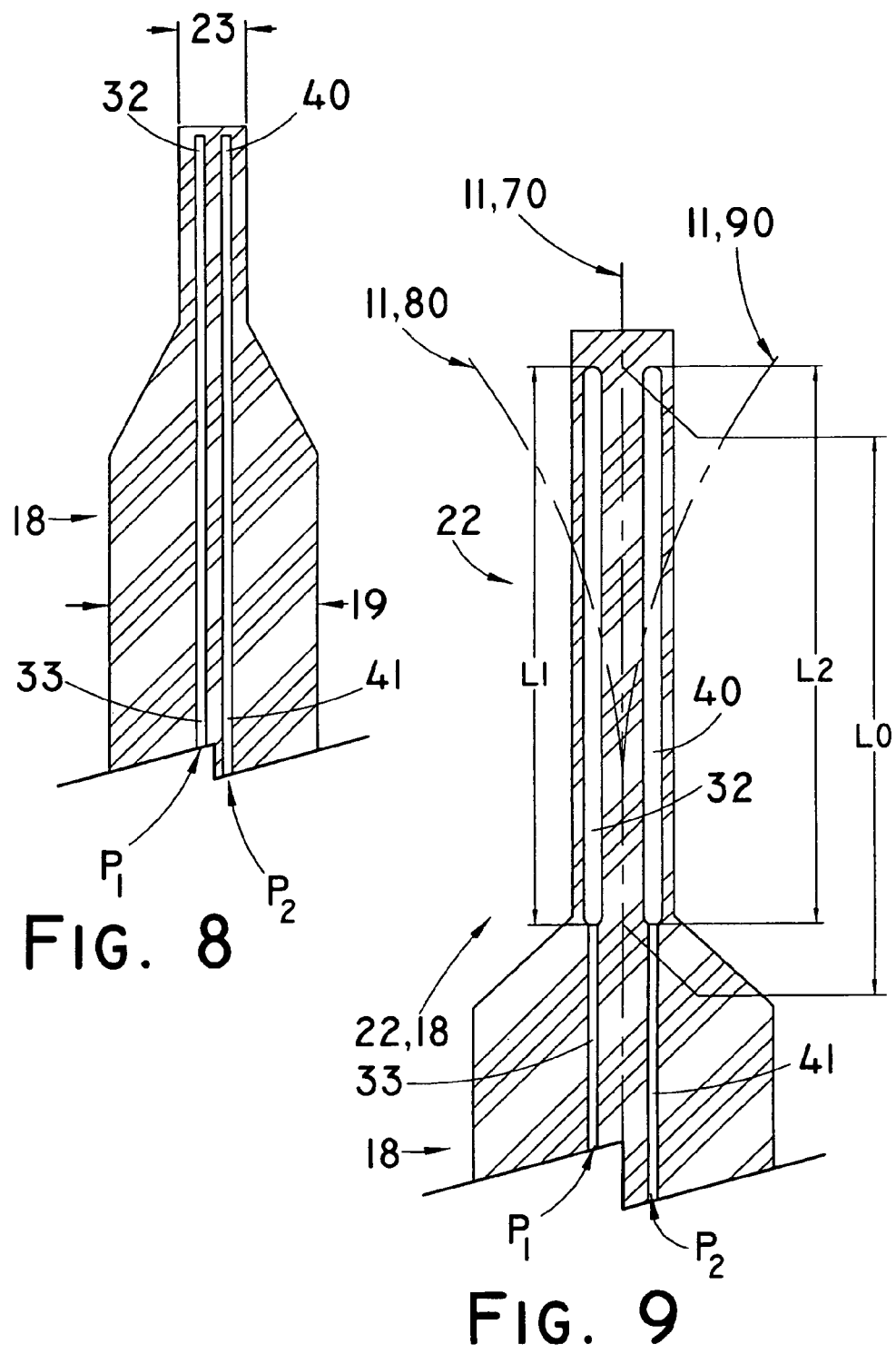
FIG. 8 is an alternative partial schematic perspective view of a second end portion of a steerable catheter device according to one embodiment of the invention.
FIG. 9 is a partial schematic side view of an alternative embodiment of a second end portion of a steerable catheter device according to one embodiment of the invention.

In one embodiment of the invention, the second end portion 18 of the catheter may comprise a radial compression resistant inner reinforcement 130. FIG. 2A provides a perspective view of a second end portion 18 of a steerable catheter device having a radial compression resistant inner reinforcement 130 according to one embodiment of the invention, although it may also represent a radial compression resistant inner reinforcement 130 of a steerable tip portion 22 (FIGS. 8 and 9). The radial compression resistant inner reinforcement 130 is configured to help inhibit radial inward expansion of a chamber body occluded end (discussed below) caused by a change in internal pressure of one or more chamber body occluded ends on the one hand, while allowing stretching, bending, articulation, and the like of the second end portion 18 and/or steering tip portion 22 on the other. The radial compression resistant inner reinforcement 130 is positioned within at least a portion of the tool receiving passageway 24 at the second end portion 18 and/or the steering tip portion 22 of the catheter 12. The radial compression resistant inner reinforcement 130 may be a layer of or comprise material of a greater durometer (e.g., harder, more stiff) compared to the distensible occluded distal end, may be a layer of or comprise an anisotropic material, or may be an internal spring, coil, mesh, wire, fiber, cannula, or other equivalent structure that allows the second end portion 18 and/or the steering tip portion 22 of the catheter 12 to bend while also resisting inward ballooning when the occluded distal end experiences a change in internal fluid pressure. By way of illustration only and not by way of limitation, the radial compression resistant inner reinforcement 130 may comprise one or a combination of the following materials: metals and alloys such as nickel-titanium alloy ("nitinol") or medical grade stainless steel.

Figure 2B:
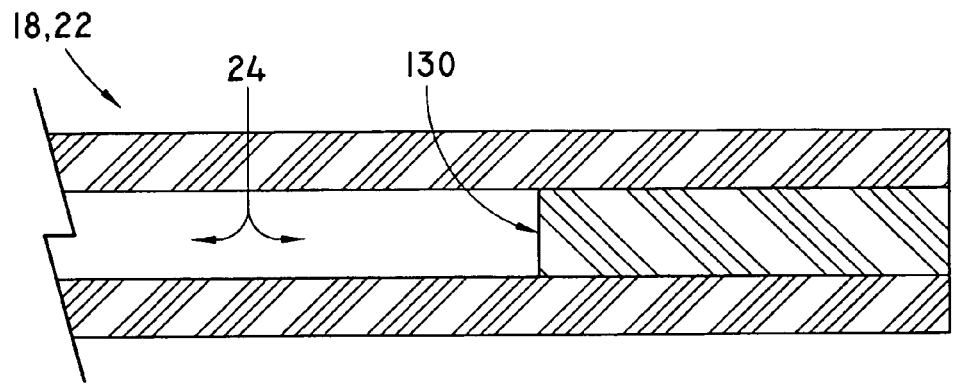
FIG. 2B provides a perspective view of an alternative embodiment of a compression resistant inner reinforcement for a steerable catheter device according to the invention.

FIG. 2B provides a perspective view of an alternative embodiment of a radial compression resistant inner reinforcement 130 of a second end portion 18 for a steerable catheter device according to the invention, although it may also represent a radial compression resistant inner reinforcement 130 of a steerable tip portion 22 (FIGS. 8 and 9). In this embodiment, the tool receiving passageway has been filled with a core section 135. The core section 135 may be used in the passageway 24 of the second end portion 18 of the embodiments shown in FIGS. 1 and 2, and may also be used in a steering tip portion 22. In one embodiment, the passageway 24 is replaced entirely with the core section 135 for inhibiting radial inward expansion of a longitudinal fluid flow channel 33, 37, 41, 45 and a an occluded end 32, 26, 40, 44 under a change in internal pressure of the channels or occluded ends on the one hand, while allowing stretching, bending, articulation, and the like of the second end portion 18 and/or steering tip portion 22 on the other.

The core section 135 may comprise a plug or other filler comprising any suitable material (natural, synthetic, plastic, rubber, metal, or combination thereof) that is rigid, strong, and resilient, although it should be understood that the material may also be pliable, elastic, and flexible. In one embodiment, the material of the core section 135 comprises a greater durometer compared to a distensible occluded distal end. In another embodiment, the core section 135 comprises a mechanical structure such as a wire or equivalent structure (natural, synthetic, plastic, rubber, metal, or combination thereof) that functions substantially the same way as a wire in the sense that it is flexible while also resisting inward ballooning of an occluded distal end that a central passageway or lumen encounter as the occluded distal end is under a change in internal pressure. The core section 135 may be inserted into the passageway 24 of the second end portion 18 and/or steerable tip portion 22, or formed integral into the distal end portion 18 and/or steerable tip portion 22, during manufacturing. If formed integral during manufacturing, the core section 135 may also be advantageous in the sense that it might take less space than a tool receiving passageway, thereby reducing the size of the second end portion 18 and/or steering tip portion 22, which is advantageous in small vessel passageways. Also, the core section 135 may comprise an anisotropic material so that it may stretch axially and allow the second end portion 18 and/or steering tip portion 22 to bend. By way of further illustration only and not by way of limitation, the core section 135 may comprise one or a combination of the following materials: metals and alloys such as nickel-titanium alloy ("nitinol") or medical grade stainless steel.

Figure 2C:
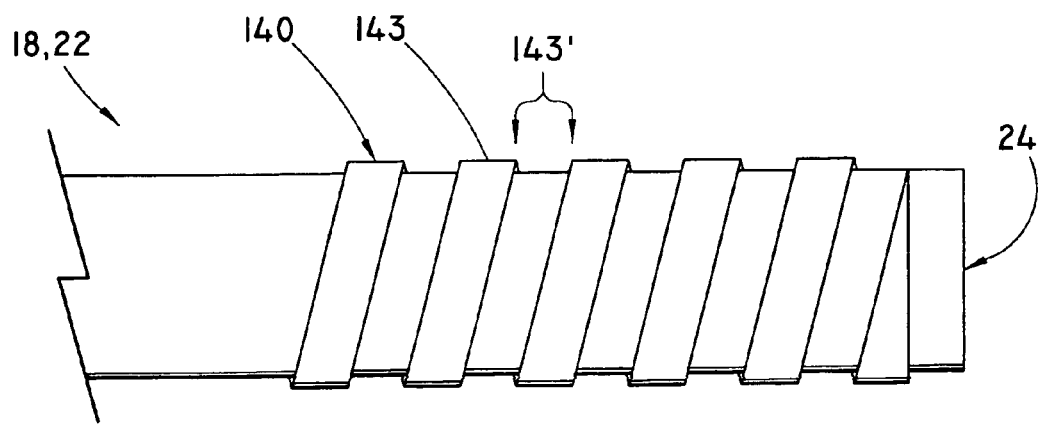
FIG. 2C provides a perspective view of a steerable catheter device having an expansion resistant outer reinforcement according to one embodiment of the invention.

FIG. 2C provides a perspective view of a second end portion 18 of a steerable catheter device having a radial expansion resistant outer reinforcement 140 according to one embodiment of the invention, although it may also represent a radial compression resistant inner reinforcement 130 of a steerable tip portion 22 (FIGS. 8 and 9). The radial expansion resistant outer reinforcement 140 is configured to help inhibit radial outward expansion of a chamber body occluded end (discussed below) caused by a change in internal pressure of one or more chamber body occluded ends on the one hand, while allowing stretching, bending, articulation, and the like of the second end portion 18 and/or steering tip portion 22 on the other. The radial expansion resistant outer reinforcement 140 is disposed about at least a portion of the second end portion outer circumference 120 at the second end portion 18 and/or the steering tip portion 22 of the catheter 12. The radial expansion resistant outer reinforcement 140 may be a layer of or comprise material of a greater durometer compared to the distensible occluded distal end, may be a layer of or comprise an anisotropic material, or may be an internal spring, coil, mesh, wire, fiber, cannula, or other that allows the second end portion 18 and/or steering tip portion 22 to bend while also resisting inward ballooning when the occluded distal end experiences a change in internal fluid pressure. By way of illustration only and not by way of limitation, the radial expansion resistant outer reinforcement 140 may comprise one or a combination of the following materials: metals and alloys such as nickel-titanium alloy ("nitinol") or medical grade stainless steel.

In one embodiment, the radial expansion resistant outer reinforcement 140 comprises a coil 143. The coil may be compression fitted or wound around the outer circumference 120 of the distal end portion 18 and/or steering tip portion 22. The coil 143 includes a plurality of turns, and preferably includes uniform spacings 143' between the turns of the coil 143. The coil 143 may be formed of any suitable material that will provide appropriate structural reinforcement, such as stainless steel flat wire or biologically compatible metals, polymers, plastics, alloys (including super-elastic alloys), or composite materials that are either biocompatible or capable of being made biocompatible. Also, the coil 143 may be a cannula that has transverse slots relative to the longitudinal axis of the cannula. The slotted cannula's transverse slots may be perpendicular to the longitudinal axis of the cannula or form an acute angle or obtuse angle relative to the longitudinal axis of the cannula.

Although the embodiment in FIG. 2C shows a flat ribbon shaped wire coil 143, coils of other cross-sectional dimensions, such as round wire, may also be used. When flat wire stainless steel is used, the coil 143 is optionally formed from wire that is about 0.003 inches thick by about 0.012 inches wide. In one embodiment, the turns of coil 143 are uniformly spaced 143' apart by approximately 0.0118 inches. While FIG. 2C shows an embodiment that uses coils 143 having uniformly spaced turns and a constant pitch, this is not required and coils 143 may be spaced 143' by non-uniform distances or at varying distances. In one embodiment, the ends of coil 143 are positioned approximately 0.197 inches proximal to the end face of the distal second end portion 18 and/or steering tip portion 22.

FIG. 1 also shows that the steerable catheter 12 comprises at least one elongate chamber body, such as any one of the chamber bodies 30, 34, 38, 42, respectively. The term chamber and variations thereof are used to describe embodiments of the invention, rather than any lexicographic definition regarding those terms. As a result, a chamber should have its plain and ordinary meaning that includes any elongated cavity or enclosed volume, space, or compartment comprising an opening.

Therefore, a catheter according to one embodiment of the present invention further comprises any one or more of the elongated chamber bodies 30, 34, 38, and 42. These chamber bodies 30, 34, 38, 42 extend approximately longitudinally from proximal openings 31, 35, 39, 43 at or near the first end portion 14 and terminating at an elastically fluid-distensible occluded distal ends 32, 36, 40, 44 (hereinafter "distensible occluded distal end(s)" and "occluded distal end(s)") (e.g., FIG. 7) within the catheter flexible distal second end portion 18. The occluded distal ends optionally may comprise an anisotropic material. Occluded distal ends 32, 36, 40, and 44 are disposed within the catheter flexible second end 18 and/or optional steering tip 22 (discussed below) and are radially offset relative to the central longitudinal axis 11 of the second end 18 and optional steering tip 22. The openings 31, 35, 39, 43 and occluded ends 32, 26, 40, 44 define and are in communication via longitudinal fluid flow channels 33, 37, 41, 45, respectively, that extend between the respective openings and occluded ends for allowing changes in internal fluid pressure to transport from the chamber proximal opening to the occluded distal end.

The distensible occluded distal ends 32, 36, 40, 44 may be any suitable length at or near the catheter second end portion 18 sufficient, when under positive or negative pressure, to distend axially (e.g., elongate longitudinally, lengthwise or shorten longitudinally, lengthwise) and thereby—individually or in conjunction with another one or more occluded distal ends under positive or negative pressure—to cause the catheter second end portion 18 to articulate. In other words, the occluded distal end 32, 36, 40, and 44 elastically distends axially under a change in internal fluid pressure (described below) and thereby articulates the catheter flexible second end portion 18 from a relaxed (e.g., neutral, substantially equal pressure) position 70 to a bending position 80, 90 as explained below (e.g., FIGS. 1 and 9). It should be understood that, where the catheter flexible second end portion 18 comprises a steering tip portion 22 as discussed below, articulating the catheter flexible second end portion 18 would articulate the steering tip portion 22, too, or may articulate the steering tip portion 22 independent of the second end portion 18.

As shown in FIGS. 3A through 3D, the at least one chamber body, such as 30, 34, 38, 42 for example, may comprise several configurations. FIG. 3A represents one illustrative embodiment wherein a distensible occluded distal end 32 is radially offset and parallel to the catheter 12 central longitudinal axis 11. FIG. 3B represents an alternative embodiment wherein distensible occluded distal end 32 is radially offset and substantially parallel to, but having a bend 32' away from, the catheter 12 central longitudinal axis 11 near the distensible occluded distal end 32. FIG. 3C represents an alternative embodiment wherein a distensible occluded distal end 32 is offset and substantially parallel to, but having a bend 32' toward, the catheter 12 longitudinal axis 11. In yet another embodiment, FIG. 3D shows a distensible occluded distal end 32 having more than one bend 32, 32' relative to the central longitudinal axis 11, and optionally a corkscrew or helical configuration. Moreover, any one or more the chamber body and/or corresponding channel may be straight or at times curved, because the second end portion 18 is flexible while the first end portion 14 and intermediate portion 16 may also be flexible.

In one embodiment, the device comprises a second elongate chamber body 30, 34, 38, 42 terminating at a second elastically fluid-distensible occluded distal end 32, 36, 40, 44 radially offset relative to the central longitudinal axis 11 and radially offset relative to the first elastically fluid-distensible occluded distal end 32, 36, 40, 44. In another embodiment, the device comprises at least a third elongate chamber body 30, 34, 38, 42 terminating at a second elastically fluid-distensible occluded distal end 32, 36, 40, 44 radially offset relative to the central longitudinal axis 11 and radially offset relative to the first and second elastically fluid-distensible occluded distal ends 32, 36, 40, 44.

Figure 4:
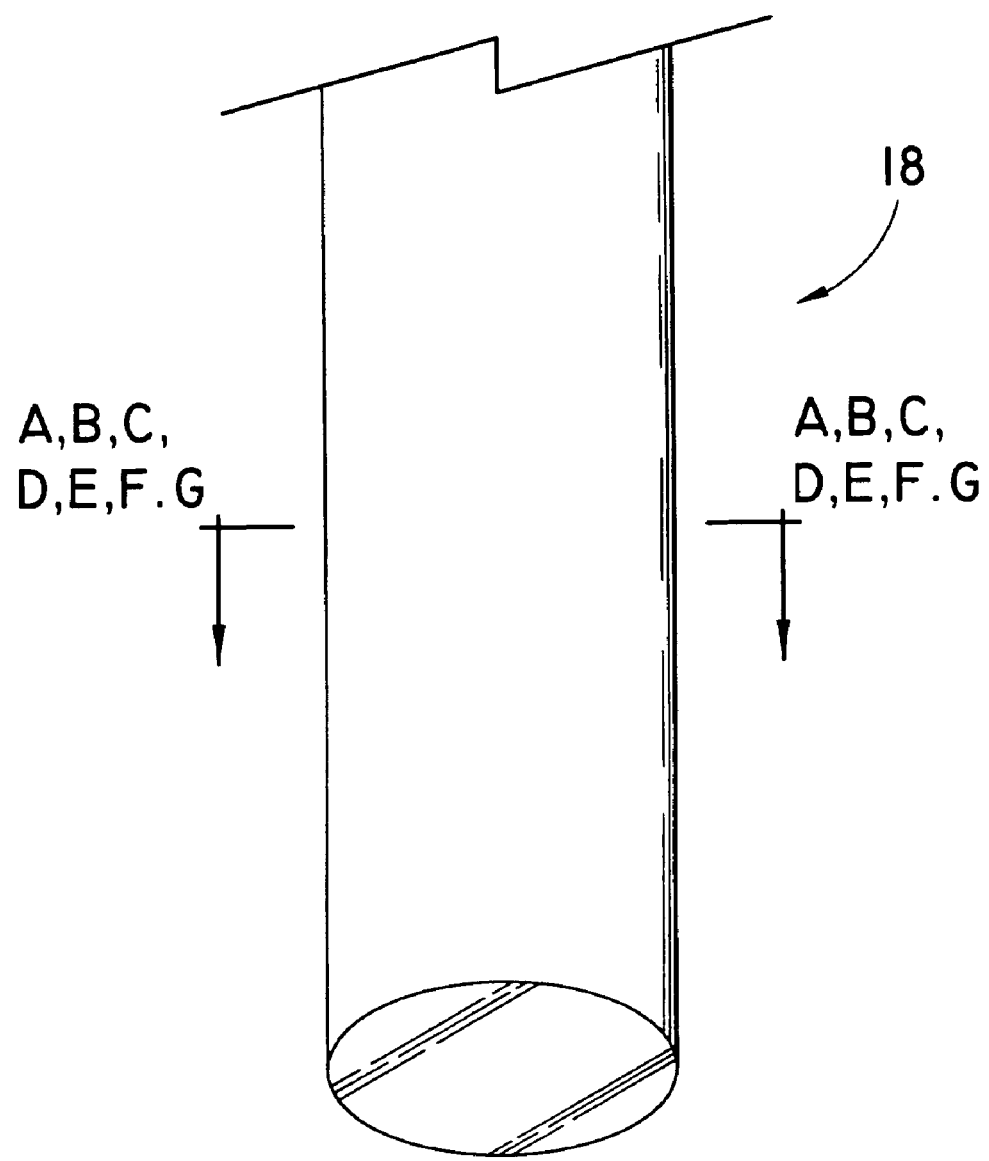
FIG. 4 provides a partial schematic view, broken away, of a steerable catheter device according to an embodiment of the invention.

FIG. 4 schematically shows the catheter flexible second end portion 18 that may have a cross section along the lines A-A, B-B, C-C, D-D, E-E, F-F, and G-G comprising a variety of suitable configurations. Any one or more of the at least one chamber body, such as 30, 34, 38, 42 for example, may comprise several configurations along any one of the chamber body longitudinal fluid flow channels 33, 37, 41, 45, respectively. For example, the cross section may be circular, square, rectangular, triangular, crescent, semi-circular, oval, elliptical, T-shaped, U-shaped, or otherwise of a curved configuration.

Figure 4A:
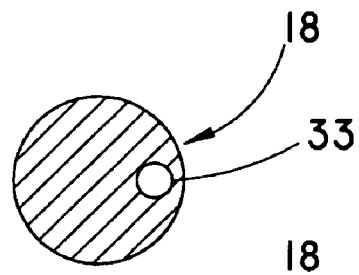
FIGS. 4A through 4G are cross sectional views of FIG. 4 taken along the lines A-A, B-B, C-C, D-D, E-E, F-F, and G-G, respectively, according to alternative embodiments of a chamber body of a flexible second end portion according to the invention.
Figure 4B:
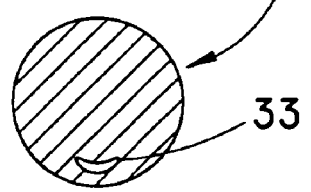
Figure 4C:
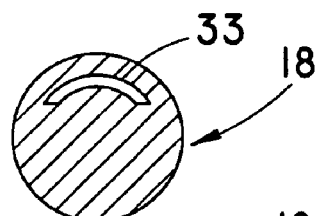
Figure 4D:
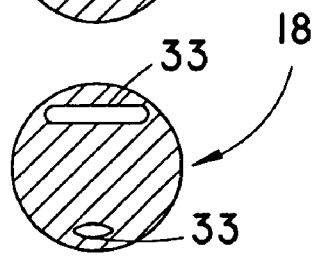
Figure 4E:
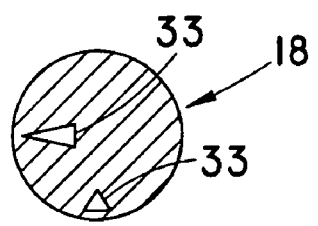
Figure 4F:
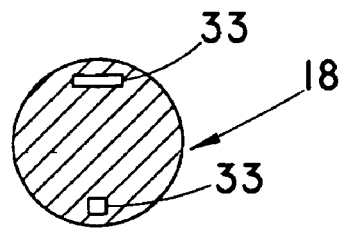
Figure 4G:
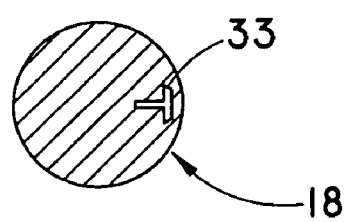

FIG. 4A, a cross sectional view of FIG. 4 taken along the lines A-A, includes a circular chamber body channel 33. FIG. 4B, a cross sectional view of FIG. 4B taken along the lines B-B, includes a crescent chamber body channel 33. FIG. 4C, a cross sectional view of FIG. 4 taken along the lines C-C, includes a semi-circular chamber body channel 33. FIG. 4D, a cross sectional view of FIG. 4 taken along the lines D-D, includes an elliptical or oval chamber body channel 33. FIG. 4E, a cross sectional view of FIG. 4 taken along the lines E-E, includes triangular chamber body channels 33. FIG. 4F, a cross sectional view of FIG. 4 taken along the lines F-F, includes a rectangular or square chamber body channel 33. FIG. 4G, a cross sectional view of FIG. 4 taken along the lines G-G, includes a T-shaped chamber body channel 33.

The occluded distal ends are elastically distensible axially under an internal fluid pressure. The fluid may be any suitable fluid. Examples of suitable fluids include, but are not limited to, air, gas, liquid, water, oil, saline solution, or combinations thereof. In one embodiment, the fluids include liquids or gases that are biocompatible or capable of being made biocompatible. The occluded distal ends may comprise any suitable elastomeric material described above, including by way of illustration and not by way of limitation elastomeric materials comprising latex, silicone, urethane, a thermoplastic elastomer, or any combinations thereof.

Figure 5A:
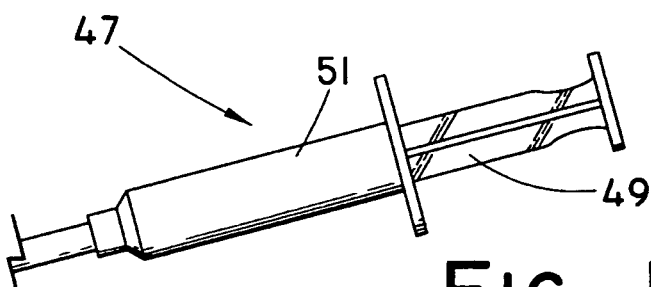
FIGS. 5A through 5C provide schematic partial views of actuators for injecting and withdrawing fluids.
Figure 5B:
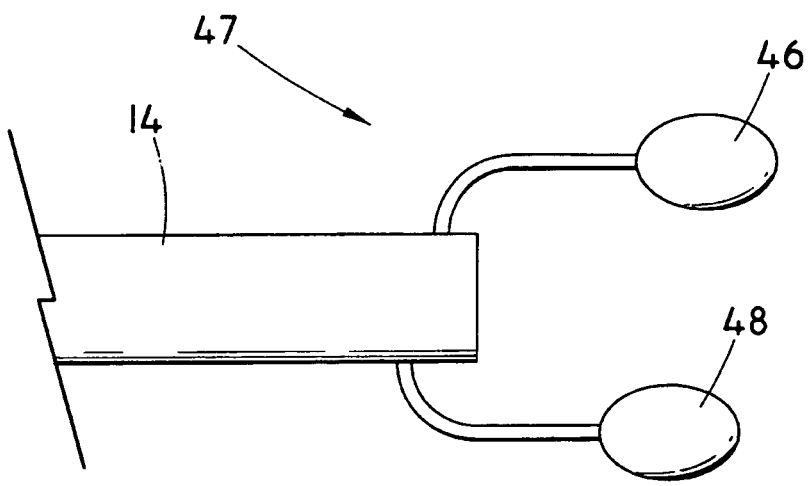
Figure 5C:
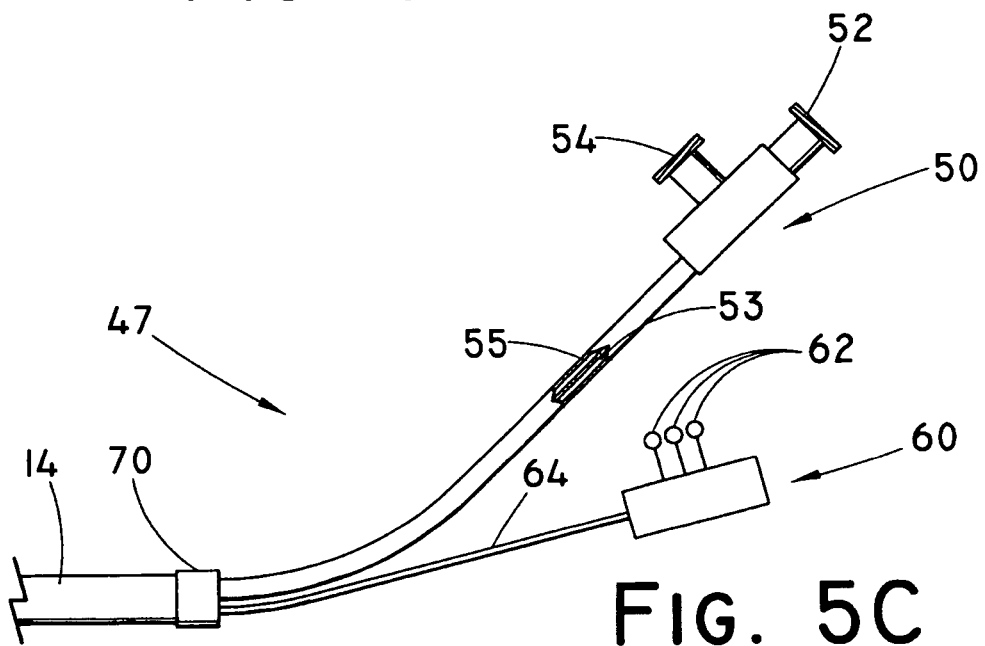

As shown in FIGS. 5A, 5B, and 5C, the present invention further comprises fluid actuators 47. These actuators may comprise any component for injecting and withdrawing fluids to articulate the second end portion 18 of a catheter and/or a steering tip portion 22 (as shown in FIGS. 8, 9). For example, the actuators may comprise mechanically operated elements, electronically operated elements, electromechanically operated elements, pneumatically operated elements, hydraulically operated elements, piezoelectrically operated elements, thermomechanically, chemomechanically operated elements, and photoelectrically operated elements.

As one skilled in the art will understand, the actuators 47 illustrated in FIGS. 5A-5C are provide by way of example and not by way of limitation. According to the present invention, the actuator 47 of FIGS. 5A and 5B depict pneumatic devices. One illustrative pneumatic device is a syringe having a plunger 49 and a barrel 51 for injecting and withdrawing fluids. Another pneumatic device is shown in FIG. 5B and comprises a plurality of inflation elements 46, 48, respectively, for injecting and withdrawing fluids, which inflation elements may include, for instance, a balloon apparatus. The pneumatic devices of FIGS. 5A and 5B may be remotely, detachably, and selectively coupled to the first end 14, or otherwise operatively coupled to be in communication with the previously described proximal openings 31, 35, 39, 43, respectively, located at or near the first end 14.

By way of example only and not by way of limitation, the terms "operatively coupling," "operatively coupled," "coupling," "coupled," and variants thereof are not used lexicographically but instead are used to describe embodiments of the invention having a point, position, region, section, area, volume, or configuration at which two or more things are mechanically, chemically, and/or chemical-mechanically bonded, joined, adjoined, connected, associated, united, mated, interlocked, conjoined, fastened, held together, clamped, crimped, friction fit, pinched, press fit tight, nested, wedged, and/or otherwise associated by a joint, a junction, a juncture, a seam, a union, a socket, a melt bond, glue, adhesives, resins, welding (laser, spot, etc.), soldering, brazing, adhesives, chemical bonding materials, implanted arrangement, or combinations thereof. The term "communication," and variants thereof as used herein, includes the passage, conveyance, injection, ventilation, flow, movement, blockage, withdrawal, evacuation, or regulation of fluids.

FIG. 5C shows two more embodiments of actuators 47. In the top portion, the actuator has a control box 50 with first and second handles 52, 54, respectively, for injecting and withdrawing fluids through first and second lumens 53, 55, respectively, leading to any two corresponding proximal openings 31, 35, 39, 43, respectively. There may be additional handles leading to the other proximal openings. In the bottom portion, the input/output unit 60 has a plurality of switches 62 that control hydraulic fluids through a hydraulic cable 64.

The actuators 47 of FIGS. 5A-5C may be used alone or in combination according to the invention. In all of these embodiments, the actuator may be located at, within a short distance to, or remotely positioned relative to the first end 14. Also, these actuators may attach directly to the openings 31, 35, 39, 43, respectively, or may operably communicate with the opening via an adaptor 65 that detachably connects to the openings and/or the first end portion 14. One example of an adaptor 65 may be a Tuohy-Borst or similar fitting that has one branch with ports in communication with the proximal openings 31, 35, 39, 43, and has a second branch for the tool receiving passageway 24. Also, these actuators may be connected to the openings at the hospital, ambulance, health care treatment location, or attached during manufacture.

Figure 6:
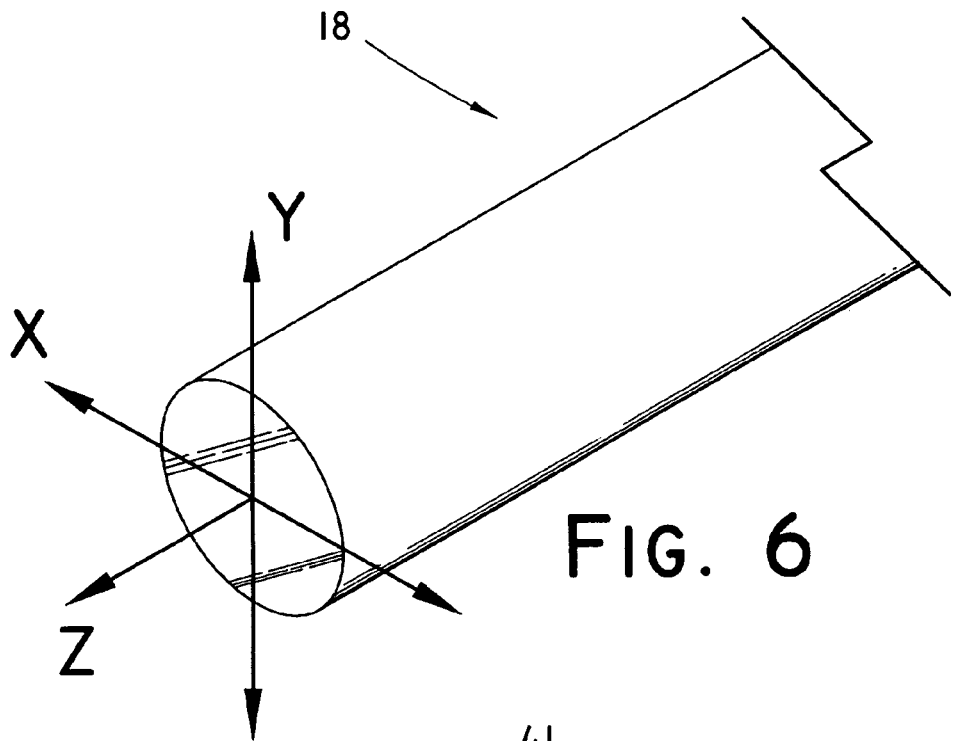
FIG. 6 provides a partial schematic perspective view of a second end portion of a steerable catheter device according to one embodiment of the invention.

FIG. 6 schematically shows (with x, y, and z axes) the catheter flexible second end portion 18 that is capable of articulating. Here, articulate means moveable and includes rotation, bending, or translational displacements along the x, y, and z axes and combinations thereof (e.g., between planes formed by the x, y, and z axes). For instance, the articulation may be axial, longitudinal, forward, backward, orthogonal, lateral, transverse, rotational, pivotable, sloping incline or decline, swinging, torsional, revolving, and other forms of translation and/or rotation in an x, y, and/or z coordinate system (collectively, "articulation," "articulate," "articulatable," "articulatively," and variants thereof).

Figure 7:
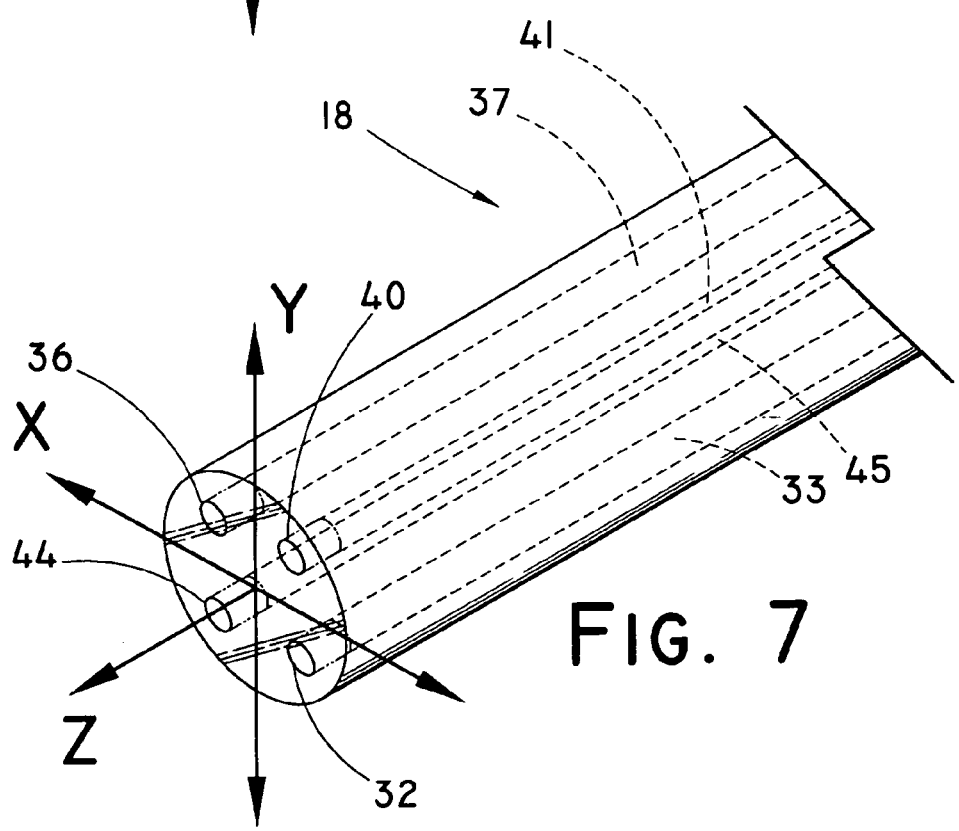
FIG. 7 is a view of FIG. 6 showing the channels and occluded ends of a steerable catheter device.

FIG. 7 shows a flexible second end portion 18 according to the invention. The second end portion 18 further comprises a plurality of longitudinal fluid flow channels 33, 37, 41, 45 providing passageways for fluids to articulate the flexible second end portion 18 and/or the steering tip portion 22 as shown in FIGS. 1, 8, 9, and 10. Each channel of the plurality of channels is in communication with a corresponding distensible occluded distal end 32, 36, 40, 44 (e.g., closed ends of the corresponding chambers) disposed within the second end portion 18 and/or steering tip portion 22. The distensible occluded distal end, as used to describe FIG. 7 and the other embodiments, may be any suitable dimension and shape, and may be any appropriate width or length sufficient to distend and, as a result, to articulate the second end portion 18 and/or steering tip portion 22.

Given the configuration of a vessel passageway to be navigated or the channel of an endoscope or accessory device, an embodiment of the catheter flexible second end portion 18 may comprise a flexible steering tip portion 22. Optionally, the flexible second end portion 18 has a proximal first outer diameter 19 and the steerable distal tip portion 22 has a second outer diameter 23 that is smaller than the first outer diameter 19. The smaller second outer diameter 23 is configured to minimize pain and discomfort and/or to reach smaller vessel passageways. Optionally, the steering tip portion 22 (see (FIGS. 8 and 9) may have a mostly tubular configuration with a distal tapered, rounded, chamfered, or arrow-head shape that may be better tolerated by the patient to minimize pain and discomfort. Further, in certain embodiments, the steering tip portion 22 may be soft, rounded, and flexible so as to provide further comfort and safety to the patient.

Depending on the intended use for the device and the particular medical procedure to be performed, one embodiment of a chamber body for a steerable catheter assembly comprises a plurality of longitudinal fluid flow channels 33, 37, 41, 45 arranged about the aforementioned passageway 24 at the second end portion 18. As used herein, the term "plurality" has its plain and ordinary meaning of two or more. Each channel of the plurality of flow channels comprises a corresponding proximal opening located at or near the first end portion 14 and a distensible occluded distal end at the steerable distal tip portion 22, defining a passageway between the opening and the closed end of the chamber (e.g., the distensible occluded distal end). The term "each," as used to describe embodiments of the invention shown in the figures, discussed in this detailed description, and recited in the claims, simply means each of the "plurality," which does not foreclose other possibilities such as, having a flow channel that lacks either an opening, a distensible occluded distal end, or both, or lacks a passageway therebetween. The term "about" shall have its plain and ordinary meaning of describing embodiments of the invention, rather than defining any claim term. Thus, the flow channel embodiments may be configured such that the two or more flow channels are positioned longitudinally around the outside, near but not necessarily contiguous, of a tool receiving passageway 24, as shown in FIG. 1.

FIG. 8 shows a longitudinal cross section of an embodiment comprising a flexible second end portion 18 having a steering tip portion 22. This embodiment discloses a plurality of channels 33, 41 providing passageways for fluids to articulate the flexible second end portion 18 and/or the steering tip portion 22. Each channel of the plurality of channels comprises a corresponding distensible occluded distal end 32, 40, respectively, located at or near the second end portion 18.

FIG. 9 is a partial perspective view of a longitudinally sectioned second end portion 18 and steering tip portion 22 showing schematically how one embodiment according to the invention works. FIG. 9 is illustrative only, and it could also represent how a steering tip portion 22 and/or second end portion 18 articulate. Moreover, although FIG. 9 shows two distensible occluded distal ends 32, 40, it could have just one distensible occluded distal end (e.g., 32 or 40) or could have more than two distensible occluded distal ends (e.g., 32, 36, 40, 44).

More particularly, where the distensible occluded distal ends 32, 40 are under an approximately equal internal pressure ($P_1=P_2$), then the steering tip portion 22 and/or second end portion 18 assume a relaxed (e.g., neutral or under a substantially equal pressure) position 70, which is substantially coaxial with the longitudinal axis 11 such that the length $L=L_1=_2=L_0$. The steering tip portion 22 and/or second end portion 18 may still articulate because it is flexible, but would do so passively (e.g., by following the curvature of the vessel passageway).

FIG. 9 further shows that where the distensible occluded distal ends 32, 40 are under an unequal internal pressure, then the steering tip portion 22 and/or second end portion 18 will articulate—by way of example and not by way of limitation—to a bending position 80, 90. These bending positions 80, 90 are for illustrative purposes only, as there may be a number of bends 80, 90 along a continuum from the relaxed (e.g., neutral or under a substantially equal pressure) position 70 to the maximum articulation allowable by the steering tip portion 22 and/or second end portion 18. The bending positions 80, 90 may range from approximately 1 degree to approximately 15 degrees relative to the neutral position, and in another embodiment from about 2 degrees to approximately 5 degrees relative to the neutral position, although the embodiments according to the invention need not achieve the entire range but simply fall within those ranges, and the bending positions may be greater if desired.

If $P_1<P_2<0$ then $L_1<L_0<L_2<L$ such that the steering tip portion 22 and/or second end portion 18 articulate toward a first bending position 80. Similarly, if $P_1<0<P_2$ then $L_1<L_0$, $L<L_2$ such that the steering tip portion 22 and/or second end portion 18 articulate toward a first bending position 80. Conversely, if $P_1>P_2>0$ then $L_1>L_0>L_2>L$ such that the steering tip portion 22 and/or second end portion 18 articulate toward a second bending position 90. Likewise, if $P_1>0>P_2$ then $L_1>L_0$, $L>L_2$, such that the steering tip portion 22 and/or second end portion 18 articulate toward a second bending position 90.

In other words, a chamber body longitudinal fluid flow channel 33, 37, 41, 45, as previously described, having a distensible occluded distal ends 32, 36, 40, 44, respectively, that is under a positive pressure (in a single chamber embodiment) or greater positive pressure relative to other distensible occluded distal ends (in an embodiment having a plurality of chambers) will distend axially (e.g., will elongate longitudinally in the lengthwise direction) and, thereby, result in articulation at the steering tip 22 and/or second end 18. Conversely, a distensible occluded distal end 32, 36, 40, and/or 44 that is under a negative pressure (in a single chamber embodiment) or greater negative pressure relative to other distensible occluded distal ends (in an embodiment having a plurality of chambers) will distend (e.g., shorten longitudinally) and, thereby, result in articulation at the steering tip 22 and/or second end 18.

It should be understood that articulation results when one or more distensible occluded distal ends is under any internal pressure differential. Thus, one distensible occluded distal end could be under either a positive or negative internal pressure sufficient to cause articulation. Also, there could be two or more distensible occluded distal end under unequal internal pressure (positive, negative, or positive and negative) sufficient to cause articulation such that one distensible occluded distal end distends (elongates longitudinally) and the other distensible occluded distal end distends (shortens longitudinally).

The steering tip portion 22 may further comprise an expansion resistant outer reinforcement 140 described above in connection with FIG. 2B. Likewise, the steering tip portion 22 may comprise a core section 135 described above in connection with FIG. 2C. In one embodiment, there is a tool receiving central passageway 24, as previously described, that is disposed within the catheter 12 and extends from a first end opening 26 to a second end opening 28, the passageway 24 being substantially coaxial with the central longitudinal axis 11 at the catheter flexible steering tip portion 22, wherein the distensible occluded distal ends 32, 40 are radially offset relative to the passageway 24 and radially offset relative to each other 32, 40 and other occluded distal ends 36, 44 if present. Alternatively, the passageway 24 may be plugged by a core section 135, as previously described, in order to provide reinforcement by uniformly inhibiting radial inward expansion of the chamber body occluded distal ends 32, 36, 40, 44. Furthermore, the passageway 24 may comprise a compression resistant inner reinforcement 130 at or near the steering tip portion 22 and occluded distal ends 32, 36, 40, 44 as described in connection with FIG. 2A.

Figure 10A:
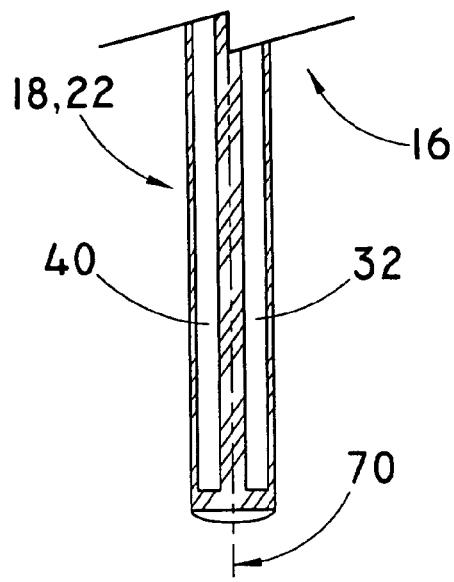
FIG. 10A is a partial schematic side view of an alternative embodiment of a second end portion of a steerable catheter device according to one embodiment of the invention shown in a relaxed position.

FIG. 10A shows an alternative embodiment of a flexible second end portion 18 and/or steering tip portion 22 and a flexible intermediate portion 16 of a steerable catheter device according to the invention having two distensible occluded distal ends 32, 40. FIG. 10A depicts two distensible occluded distal ends 32, 40 before any internal pressure differential, so the flexible second end portion 18 and/or steering tip portion 22 is in a relaxed (e.g., neutral or under a substantially equal pressure) position 70. While FIG. 10A shows distensible occluded distal ends 32, 40, it should be understood that FIG. 10A could have one, two, or more distensible occluded distal ends.

Figure 10B:
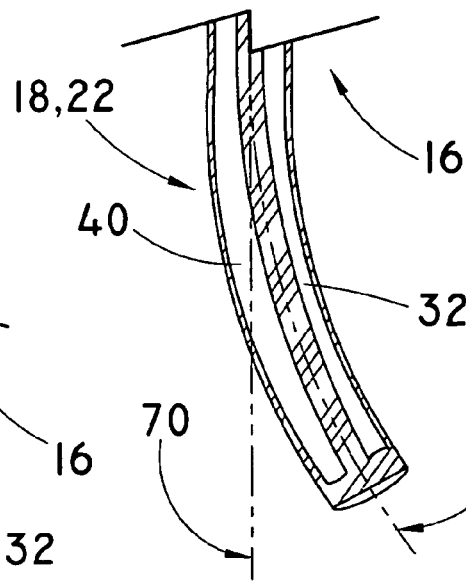
FIGS. 10B and 10C illustrate FIG. 10A articulating under an internal fluid pressure.

FIG. 10B shows the second end portion 18 and/or steering tip portion 22 articulating when at least one or more distensible occluded distal end is under an unequal internal pressure. The second end portion 18 and/or steering tip portion 22 are shown to be capable of articulating to a bending position 80 relative to the neutral position 70. Thus, if the occluded distal end 40 is under positive pressure, then it will distend (here it is shown elongating longitudinally relative to the distensible occluded distal end 32) and the catheter second end portion 18 and/or steering tip portion 22 articulates to the bending position 80. This result could also be achieved by creating a negative pressure in the distensible occluded distal end 32 such that it distends (e.g., shortens longitudinally relative to the distensible occluded distal end 40). Additionally, the second end portion 18 and/or steering tip portion 22 could articulate as a result of a negative pressure in the distensible occluded distal end 32 and a positive pressure in the distensible occluded distal end 40.

Figure 10C:
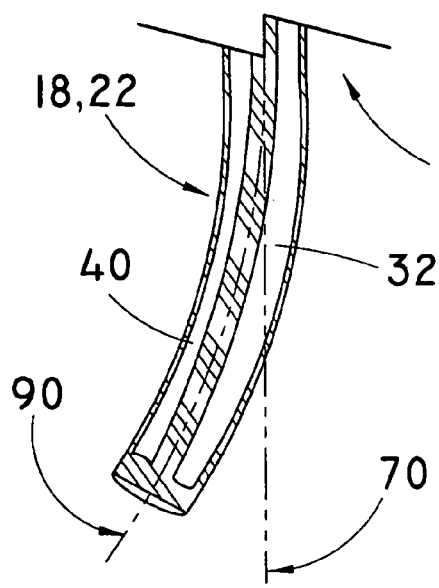

FIG. 10C shows the second end portion 18 and/or steering tip portion 22 articulating to the left when at least one or more distensible occluded distal end is under an unequal internal pressure. The second end portion 18 and/or steering tip portion 22 are shown to be capable of articulating to a bending position 90 relative to the neutral position 70. Thus, if the occluded distal end 32 is under positive pressure, then it will distend (here it is shown elongating longitudinally relative to the distensible occluded distal end 40) and the catheter second end portion 18 and/or steering tip portion 22 articulates to the bending position 90. This result could also be achieved by creating a negative pressure in the distensible occluded distal end 40 such that it distends (e.g., shortens longitudinally relative to the distensible occluded distal end 32). Additionally, the second end portion 18 and/or steering tip portion 22 could articulate as a result of a negative pressure in the distensible occluded distal end 40 and a positive pressure in the distensible occluded distal end 32.

Methods of orienting a surgical access catheter device are also provided. FIG. 11 shows one embodiment of the method 100 according to the invention. For example, a method according to the invention comprises providing (step 101) a catheter having a first end 14, an elongate intermediate portion 16, and a flexible second end 18 (and/or steering tip 22) defining a central longitudinal axis 11, a dye injection lumen 124, a tool receiving passageway 24, a plurality (e.g., two or more) of elongate chamber bodies 30, 34, 38, 42 having a proximal opening 31, 35, 39, 43 at or near the first end 14 and terminating at an axially distensible occluded distal end 32, 36, 40, 44, respectively, within the catheter flexible second end 18 (and/or steering tip 22) and defining a fluid flow channel 33, 37, 41, 45, respectively, therebetween, the occluded distal end 32, 36, 40, 44 being radially offset relative to the central longitudinal axis 11 and being substantially straight in a relaxed (e.g., neutral and/or relaxed (e.g., neutral, approximately equal pressure) position 70 and bent to a bending position 80, 90 under a change in internal fluid pressure.

A fluid actuator 47 capable of controlling a supply of fluid is provided (step 102) and operably connected (step 103) at or near the catheter first end in operable communication with at least one of the proximal openings of at least one of the two or more chamber bodies. The fluid actuator is operated (step 104) to control the fluid supply within the occluded distal end, the flexible second end is selectively articulated (step 105) in response to a change of fluid pressure within the occluded distal end. It should be understood in describing the methods according to the invention that the flexible second end 18 may comprise a steering tip portion 22 containing the occluded distal end that selectively articulates the steering tip portion 22 in response to a change of fluid pressure within the occluded distal end. As such, for purposes of the method claims the second end 18 may be considered a steering tip portion 22.

In one embodiment, a steering tip portion 22 is provided (step 106). The steering tip portion extends distally from the flexible second end 18, wherein the intermediate portion 16 has a first outer diameter 15 and the steering tip portion 22 has a second outer diameter 19 that is smaller than the first diameter 15.

In one embodiment, a tool receiving passageway 24 is provided (step 108). A wire guide is received (step 110) within the tool receiving passageway 24.

In another embodiment, a compression resistant inner reinforcement 130, 135 is provided (step 112), the inner reinforcement 130, 135 being positioned within at least a portion of the tool receiving passageway 24 at the second end portion 18 and/or the steering tip portion 22 of the catheter 12 and being configured to help inhibit radial inward expansion of a chamber body occluded end (discussed below) caused by a change in internal pressure of one or more chamber body occluded ends on the one hand, while allowing stretching, bending, articulation, and the like of the second end portion 18 and/or steering tip portion 22 on the other. Also, an expansion resistant outer reinforcement 140 may be provided (step 114), the outer reinforcement 140 disposed about at least a portion of the second end portion outer circumference 120 at the second end portion 18 (for purposes of the description of the embodiment, the second end portion 18 may be considered as including the steering tip portion 22) and being configured to help inhibit radial outward expansion of a chamber body occluded end caused by a change in internal pressure of one or more chamber body occluded ends on the one hand, while allowing stretching, bending, articulation, and the like of the second end portion 18 and/or steering tip portion 22 on the other.

The method 100 further comprises a selectively articulating step wherein fluid is supplied into the chamber body proximal opening (31, 35, 39, 43), through the fluid flow channel (33, 37, 41, 45), and into the axially distensible occluded distal end (32, 36, 40, 44). Supplying the fluid to the occluded distal end creates a positive pressure in the occluded distal end and thereby axially distends distally the occluded distal end so as to articulate the catheter flexible second end portion from the relaxed position to the bending position.

The method 100 further comprises a selectively articulating step comprises wherein fluid is aspirated from the chamber body proximal opening (31, 35, 39, 43), the fluid flow channel (33, 37, 41, 45), and the distensible occluded distal end (32, 36, 40, 44). Aspirating the fluid from the occluded distal end creates a negative pressure in the occluded distal end and thereby axially shortens proximally the occluded distal end so as to articulate the catheter flexible second end portion from the relaxed position to the bending position.

A method of orienting a surgical access catheter device does not need to be performed sequentially. For instance, the fluid actuator may be provided (step 102) prior to providing a catheter (step 101). Likewise, steps may be combined. For example, a catheter may be provided (step 101) with a fluid actuator already connected (step 103) thereto.

It is intended that the foregoing detailed description of the medical devices be regarded as illustrative rather than limiting, and that it be understood that it is the following claims, including all equivalents, that are intended to define the spirit and scope of this invention. Terms are to be given their reasonable plain and ordinary meaning. Also, the embodiment of any figure and features thereof may be combined with the embodiments depicted in other figures. Other features known in the art and not inconsistent with the structure and function of the present invention may be added to the embodiments.

While particular elements, embodiments and applications of the present invention have been shown and described, it will be understood, of course, that the invention is not limited thereto since modifications may be made by those skilled in the art, particularly in light of the foregoing teachings. Therefore, it is therefore contemplated by the appended claims to cover such modifications as incorporate those features which come within the spirit and scope of the invention.

What is claimed is:

1. A steerable catheter assembly comprising:

a catheter having an elongated intermediate portion extending between a proximal first end portion and a distal flexible second end portion, a flexible steerable distal tip portion extending distally from the distal second end portion and an expansion resistant distally tapering portion there between, the flexible steerable distal tip having a substantially solid central core section, the first and second end portions defining a central longitudinal axis extending through the core section, the flexible second end portion having a first outer diameter and the flexible steerable distal tip portion having a second outer diameter that is smaller than the first outer diameter;

an elongate chamber body having a proximal opening located at or near the catheter first end portion and terminating at an elastically fluid-distensible occluded distal end formed integral within the flexible steerable distal tip portion, the elongate chamber body proximal opening and elongate chamber body distensible occluded distal end defining a longitudinal fluid flow channel that extends longitudinally between and in communication with the elongate chamber body proximal opening and the elongate chamber body occluded distal end, the longitudinal fluid flow channel being configured to transmit fluid to the elastically fluid-distensible occluded distal end of the elongate chamber body, the elastically fluid-distensible occluded distal end being radially offset and substantially parallel to the catheter central longitudinal axis, the elastically fluid-distensible occluded distal end is configured to distend from a neutral position to a lengthened bending position; and a fluid flow actuator operatively coupled at or near the catheter first end portion in communication with the proximal opening of the elongate chamber body, the fluid flow actuator configured to control fluid supply to the elongate chamber body occluded distal end, wherein the central core section is configured to inhibit radial inward expansion of the elastically fluid-distensible occluded distal end when the fluid flow actuator supplies fluid thereto, wherein the elongate chamber body occluded distal end is configured to elastically distend axially under a change in internal fluid pressure without substantially changing the catheter flexible steering tip portion outer diameter and thereby configured to articulate the catheter flexible steering tip portion from a substantially straight relaxed position to a bending position in response to a change of fluid pressure.

2. The device of claim 1 further comprising a radial expansion resistant outer reinforcement positioned circumferentially about the flexible steerable distal tip portion and configured to allow axial distension of the elastically fluid-distensible occluded distal end without substantial outward radial expansion of the occluded distal end.

3. The device of claim 2 wherein the radial expansion resistant outer reinforcement is selected from the group consisting of a coil, spring, wire, fiber, mesh, increased durometric material relative to the chamber body occluded distal end, anisotropic material, and a slotted cannula.

4. The device of claim 1 further comprising a dye injection lumen comprising a proximal opening located at or near the proximal first end portion of the catheter and a distal end opening located at or near the flexible steerable distal tip portion of the catheter.

5. The device of claim 1 further comprising a tool receiving passageway disposed within the catheter and extending from a first opening at or near the proximal first end portion of the catheter and a second opening at the distal flexible second end portion, the passageway being substantially coaxial with the central longitudinal axis at the proximal first end portion of the catheter.

6. The device of claim 1 wherein elastically fluid-distensible occluded distal end comprises a substantially circular cross section in the neutral position.

7. The device of claim 1 wherein elastically fluid-distensible occluded distal end comprises a substantially non-uniform cross section in the neutral position.

8. The device of claim 1 wherein the flexible steerable distal tip portion of the catheter comprises an anisotropic material that is more compliant in the axial direction than it is in the transverse direction.

9. The device of claim 1 wherein the fluid actuator further comprises an actuation mechanism selected from the group consisting of mechanically operated elements, electronically operated elements, electromechanically operated elements, pneumatically operated elements, hydraulically operated elements, piezoelectrically operated elements, thermomechanically, chemomechanically operated elements, and photoelectrically operated elements.

10. The device of claim 1 further comprising a second elongate chamber body terminating at a second elastically fluid-distensible occluded distal end positioned within the flexible steerable distal tip portion.

11. The device of claim 10 wherein the second elongate chamber body comprises a second proximal opening located at or near the catheter first end portion, the second elastically fluid-distensible occluded distal end formed integral within the flexible steerable distal tip portion and radially offset and substantially parallel to the catheter central longitudinal axis and non-axial to the first elastically fluid-distensible occluded distal end such that the catheter central longitudinal axis of the core section of the catheter flexible steerable distal tip portion is positioned between the first and second elastically fluid-distensible occluded distal ends, the second elastically fluid-distensible occluded distal end being configured to distend from the neutral position to a second lengthened bending position.

12. The device of claim 11 wherein the fluid flow actuator is operatively coupled at or near the catheter first end portion in communication with at least the first and second elongate chamber body proximal openings, the fluid flow actuator configured to control fluid supply to at least the first and second fluid flow channels and corresponding first and second elongate chamber body occluded distal ends.

13. The device of claim 11 further comprising third elongate chamber body having a third proximal opening located at or near the catheter first end portion and terminating at a third elastically fluid-distensible occluded distal end positioned within the flexible steerable distal tip portion, the third elongate chamber body proximal opening and third elongate chamber body distensible occluded distal end defining a third longitudinal fluid flow channel that extends longitudinally between and in communication with the third elongate chamber body proximal opening and the third elongate chamber body occluded distal end, the third longitudinal fluid flow channel chamber being configured to transmit fluid to the third elastically fluid-distensible occluded distal end of the elongate chamber body, the third elastically fluid-distensible occluded distal end formed integral within the flexible steerable distal tip portion and being radially offset and substantially parallel relative to the catheter central longitudinal axis of the core section such that the first, second, and third elastically fluid-distensible occluded distal ends are non-axial.

14. The device of claim 13 further comprising a fourth elongate chamber body having a fourth proximal opening located at or near the catheter first end portion and terminating at a fourth elastically fluid-distensible occluded distal end positioned within the flexible steerable distal tip portion, the fourth elongate chamber body proximal opening and fourth elongate chamber body distensible occluded distal end defining a fourth longitudinal fluid flow channel that extends longitudinally between and in communication with the fourth elongate chamber body proximal opening and the fourth elongate chamber body occluded distal end, the fourth longitudinal fluid flow channel chamber being configured to transmit fluid to the fourth elastically fluid-distensible occluded distal end of the elongate chamber body, the fourth elastically fluid-distensible occluded distal end formed integral within the flexible steerable distal tip portion and being radially offset and substantially parallel relative to the catheter central longitudinal axis of the core section such that the first, second, third, and fourth elastically fluid-distensible occluded distal ends are non-axial.

15. The device of claim 13 wherein the fluid flow actuator is operatively coupled at or near the catheter first end portion in communication with at least two of the first, second, and third elongate chamber body proximal openings, the fluid flow actuator configured to control fluid supply to at least two of the first, second, and third fluid flow channels and corresponding first, second, and third elongate chamber body occluded distal ends.

16. The device of claim 14 wherein the fluid flow actuator is operatively coupled at or near the catheter first end portion in communication with at least two of the first, second, third, and fourth elongate chamber body proximal openings, the fluid flow actuator configured to control fluid supply to at least two of the first, second, third, and fourth fluid flow channels and corresponding first, second, third, and fourth elongate chamber body occluded distal ends.

* * * * *